(12) United States Patent
Chen et al.

(10) Patent No.: US 10,388,036 B2
(45) Date of Patent: Aug. 20, 2019

(54) COMMON-MASK GUIDED IMAGE RECONSTRUCTION FOR ENHANCED FOUR-DIMENSIONAL CONE-BEAM COMPUTED TOMOGRAPHY

(71) Applicant: University of Florida Research Foundation, Incorporated, Gainesville, FL (US)

(72) Inventors: Yunmei Chen, Gainesville, FL (US); Hao Zhang, Gainesville, FL (US); Chunjoo Park, Gainesville, FL (US); Bo Lu, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 206 days.

(21) Appl. No.: 15/551,775

(22) PCT Filed: Feb. 18, 2016

(86) PCT No.: PCT/US2016/018437
§ 371 (c)(1),
(2) Date: Aug. 17, 2017

(87) PCT Pub. No.: WO2016/134127
PCT Pub. Date: Aug. 25, 2016

(65) Prior Publication Data
US 2018/0025510 A1    Jan. 25, 2018

Related U.S. Application Data

(60) Provisional application No. 62/118,952, filed on Feb. 20, 2015.

(51) Int. Cl.
*G06K 9/00*    (2006.01)
*G06T 11/00*    (2006.01)
(Continued)

(52) U.S. Cl.
CPC .............. *G06T 11/005* (2013.01); *A61B 6/03* (2013.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

| 2011/0092793 | A1 | 4/2011 | Thomson et al. |
| 2011/0176723 | A1 | 7/2011 | Ali et al. |
| 2011/0295113 | A1 | 12/2011 | Profio et al. |

OTHER PUBLICATIONS

International Search Report and Written Opinion for International Application No. PCT/US2016/18437 dated Apr. 29, 2016.
(Continued)

*Primary Examiner* — Atiba O Fitzpatrick
(74) *Attorney, Agent, or Firm* — Alston & Bird LLP

(57) ABSTRACT

A system for constructing images representing a 4DCT sequence of an object from a plurality of projections taken from a plurality of angles with respect to the object and at a plurality of times, first portions of the object being less static than second portions of the object. The system may comprise a processor configured to: iteratively process projections of the plurality of projections for a plurality of groups, each group comprising projections collected while the first portions of the object are in corresponding locations, with each iteration comprising: reconstructing first image portions representing the first portions of the object, the reconstructing of each first image portion of the first image portions being based on projections in a respective group of the plurality of groups; and reconstructing the second image portion, the second image portion representing the second portions of the object, based on projections in multiple
(Continued)

groups of the plurality of groups and on the reconstructed first image portions.

20 Claims, 11 Drawing Sheets

(51) Int. Cl.
    *A61B 6/03* (2006.01)
    *A61B 6/00* (2006.01)
(52) U.S. Cl.
    CPC ............... *A61B 6/486* (2013.01); *A61B 6/50* (2013.01); *A61B 6/5205* (2013.01); *A61B 6/5288* (2013.01); *A61B 6/583* (2013.01); *G06T 11/006* (2013.01); *G06T 11/008* (2013.01); *G06T 2211/424* (2013.01)

(56) References Cited

OTHER PUBLICATIONS

International Preliminary Report on Patentability for International Application No. PCT/US2016/018437 dated Aug. 31, 2017.
Barzilai et al., 2-Point step size gradient methods. Ima. J. Numer. Anal. 1988;8:141-8.
Bergner et al., An investigation of 4D cone-beam CT algorithms for slowly rotating scanners. Med. Phys. 2010;37:5044-53.
Bergner et al., Autodaptive phase-correlated (AAPC) reconstruction for 4D CBCT. Med. Phys. 2009;36:5695-706.
Bissonnette et al., Cone-beam computed tomographic image guidance for lung cancer radiation therapy. Int. J. Radiat. Oncol. Biol. Phys. 2009;73:927-34.
Brenner et al., Estimated radiation risks potentially associated with full-body CT screening. Radiology. 2004;232:735-8.
Brix et al., Radiation exposures of cancer patients from medical X-rays: how relevant are they for individual patients and population exposure? Eur. J. Radiol. 2009;72:342-7.
Cai et al., The effect of respiratory motion variability and tumor size on the accuracy of average intensity projection from four-dimensional computed tomography: an investigation based on dynamic MRI. Med. Phys. 2008;35:4974-4981.
Chen et al., Prior image constrained compressed sensing (PICCS). Proc. Soc. Photo. Opt. Instrum. Eng. 2008;6585:p. 15.
Chen et al., Prior image constrained compressed sensing(PICCS): a method to accurately reconstruct dynamic CT images from highly undersampled projection data sets. Med. Phys. 2008;35:660-3.
Clements et al., The effect of irregular breathing patterns on internal target volumes in four-dimensional CT and cone-beam CT images in the context of stereotactic lung radiotherapy. Med. Phys. 2013;40:11 pages.
Dawson et al., Advances in image-guided radiation therapy. J. Clin. Oncol. 2007;25:938-46.
Dietrich et al., Linac-integrated 4D cone beam CT: first experimental results. Phys. Med. Biol. 2006;51:2939-52.
Feldkamp et al., Practical cone-beam algorithm. J. Opt. Soc. Am. A. 1984;1:612-9.
Figueiredo et al., Gradient Projection for Sparse Reconstruction: Application to Compressed Sensing and Other Inverse Problems. IEEE. J. Sel. Top. Signal Process. 2007;1:586-97.
Fu et al., A cone beam CT-guided online plan modification technique to correct interfractional anatomic changes for prostate cancer IMRT treatment. Phys. Med. Biol. 2009;54:1691-1703.
Fuller et al., Method comparison of automated matching software-assisted cone-beam CT and stereoscopic kilovoltage x-ray positional verification image-guided radiation therapy for head and neck cancer: a prospective analysis. Phys. Med. Biol. 2009;54:7401-7415.
Hall, Lessons we have learned from our children: cancer risks from diagnostic radiology. Pediatr. Radiol. 2002;32:700-6.
Hatton et al., Cone beam computerized tomography: the effect of calibration of the Hounsfield unit number to electron density on Dose calculation accuracy for adaptive radiation therapy. Phys. Med. Biol. 2009;54:N329-346.
Jaffray et al., Flat-panel conebeam computed tomography for image-guided radiation therapy. Int. J. Radiat. Oncol. Biol. Phys. 2002;53:1337-49.
Jaffray, Emergent technologies for 3-dimensional image-guided radiation delivery. Semin. Radiat. Oncol. 2005;15(3):208-16.
Jia et al., Four-dimensional cone beam CT reconstruction and enhancement using a temporal nonlocal means method. Med. Phys. 2012;39:5592-602.
Kriminski et al., Respiratory correlated cone-beam computed tomography on an isocentric C-arm. Phys. Med. Biol. 2005;50:5263-5280.
Lauzier et al., Characterization of statistical prior image constrained compressed sensing.I. Application to time-resolved contrast-enhanced CT. Med. Phys. 2012;39:5930-948.
Lauzier et al., Characterization of statistical prior image constrained compressed sensing(PICCS): II. Application to dose reduction. Med. Phys. 2013;40. 15 pages.
Leng et al., High temporal resolution and streak-free four-dimensional cone-beam computed tomography. Phys. Med. Biol. 2008;53:5653-5673.
Leng et al., Streaking artifacts reduction in four-dimensional cone-beam computed tomography. Med. Phys. 2008;35:4649-59.
Li et al., Enhanced 4D cone-beam CT with inter-phase motion model. Med. Phys. 2007;34:3688-95.
Li et al., Four-dimensional cone-beam computed tomography using an on-board imager. Med. Phys. 2006;33:3825-3833.
Lubner et al., Reduced image noise at low-dose multidetector CT of the abdomen with prior image constrained compressed sensing algorithm. Radiology. 2011; 260:248-56.
Mckinnon et al., Towards imaging the beating heart usefully with a conventional CT scanner. IEEE Trans. Biomed. Eng. 1981;28:123-7.
Nakagawa et al., 4D registration and 4D verification of lung tumor position for stereotactic volumetric modulated arc therapy using respiratory-correlated cone-beam CT. J. Radiat. Res. 2013;54:152-6.
Nett et al., Tomosynthesis via total variation minimization reconstruction and prior image constrained compressed sensing (PICCS) on a C-arm system. Proc. Soc. Photo. Opt. Instrum. Eng. 2008;6913:14 pages.
Niu et al., Accelerated barrier optimization compressed sensing (ABOCS) for CT reconstruction with improved convergence. Phys. Med. Biol. 2014;59:1801-14.
Niu et al., Accelerated barrier optimization compressed sensing (ABOCS) reconstruction for cone-beam CT: phantom studies. Med. Phys. 2012;39:4588-98.
Pan et al., Why do commercial CT scanners still employ traditional, filtered back-projection for image reconstructions? Inverse. Probl. 2009;25:50 pages.
Park et al., Fast compressed sensing-based CBCT reconstruction using Barzilai-Borwein formulation for application to on-line IGRT. Med. Phys. 2012;39:1207-17.
Park et al., Four-dimensional cone-beam computed tomography and digital tomosynthesis reconstructions using respiratory signals extracted from transcutaneously inserted metal markers for liver SBRT. Med. Phys. 2011;38:1028-36.
Park et al., Liver motion during cone beam computed tomography guided stereotactic body radiation therapy. Med. Phys. 2012;39:6431-6442.
Park et al., Motion-map constrained image reconstruction (MCIR): Application to four-dimensional cone-beam computed tomography. Med. Phys. 2013;40(12):13 pages.
Park et al., Ultra-fast digital tomosynthesis reconstruction using general-purpose GPU programming for image-guided radiation therapy. Technol. Cance. Res. T. 2011;20:295-306.
Ramirez-Giraldo et al., Nonconvex prior image constrained compressed sensing (NCPICCS): theory and simulations on perfusion. CT. Med. Phys. 2011;38:2157-2167.

(56) References Cited

OTHER PUBLICATIONS

Song et al., A low-complexity 2-point step size gradient projection method with selective function evaluation for smoothed total variation based CBCT reconstructions. Phys. Med. Biol. 2014;59:6565-82.

Sonke et al., Frameless stereotactic body radiotherapy for lung cancer using four-dimensional cone beam CT guidance. Int. J. Radiat. Oncol. Biol. Phys. 2009;74:567-74.

Sonke et al., Respiratory correlated cone beam CT. Med. Phys. 2005;32:1176-86.

Sonke et al., Variability of four-dimensional computed tomography patient models. Int. J. Radiat. Oncol. Biol. Phys. 2008;70:590-8.

Szczykutowicz et al., Dual energy CT using slow kVp switching acquisition and prior image constrained compressed sensing. Phys. Med. Biol. 2010;55:6411-6429.

Tang et al., Performance comparison between total variation (TV)-based compressed sensing and statistical iterative reconstruction algorithms. Phys. Med. Biol. 2009;54:5781-804.

Wang et al., Inverse determination of the penalty parameter in penalized weighted least-squares algorithm for noise reduction of low-dose CBCT. Med. Phys. 2011;38:4066-72.

Xing et al., Overview of image-guided radiation therapy. Med. Dosim. 2006;31:91-112.

Xu et al., Detection of intrafractional tumour position error in radiotherapy utilizing cone beam computed tomography. Radiother. Oncol. 2008;89:311-19.

Yan et al., A hybrid reconstruction algorithm for fas and accurate 4D cone beam CT imaging. Med. Phys. 2013;41. 13 pages.

Yoo et al., Dosimetric feasibility of cone-beam CT-based treatment planning compared to CT-based treatment planning. Int. J. Radiat. Oncol. Biol. Phys. 2006;66:1553-1561.

Zhang et al., Correction of motion artifacts in cone-beam CT using a patient specific respiratory motion model. Med. Phys. 2010;37:2901-9.

Zhu et al., Search for IMRT inverse plans with piecewise constant fluence maps using compressed sensing techniques. Med. Phys. 2009;36:1895-1905.

COMMON-MASK GUIDED IMAGE RECONSTRUCTION FOR ENHANCED FOUR-DIMENSIONAL CONE-BEAM COMPUTED TOMOGRAPHY

RELATED APPLICATIONS

This application is a U.S. National Stage application under 37 U.S.C. § 371 based on International Application No. PCT/US2016/018437, filed Feb. 18, 2016, which claims priority under 35 U.S.C. § 119(e) to U.S. Provisional Application Ser. No. 62/118,952, titled "COMMON-MASK GUIDED IMAGE RECONSTRUCTION FOR ENHANCED FOUR-DIMENSIONAL CONE-BEAM COMPUTED TOMOGRAPHY" and filed on Feb. 20, 2015, the entire disclosures of which are herein incorporated by reference.

BACKGROUND

In modern external beam radiation therapy, the cone-beam computed tomography (CBCT) system is the most commonly used imaging modality for patient position verification during the treatment process [1-5]. By matching three dimensional (3D) CBCT volumetric images to the planned CT, the patient's treatment position can be determined accurately, and subsequently, setup parameters can be adjusted to deliver the intended treatment [6-8]. Moreover, CBCT plays a crucial role in adaptive radiotherapy by providing information on patient position and anatomical variation [1, 2, 9-12].

In addition to 3D volumetric imaging, the utilization of respiratory correlated four-dimensional (4D) imaging schemes, such as 4DCBCT, have also recently become available [8, 13-16]. 4DCBCT images represent a sequence of images, formed at successive times, which therefore can illustrate moving portions of an object being imaged. 4DCBCT allows clinicians to visualize and verify tumor motion as well as organ motion prior to the radiotherapy treatment [17, 18]. Compared to 3DCBCT, 4DCBCT can not only provide tumor motion trajectories during the respiratory process, but it can also significantly reduce motion artifacts on the images. Thus, the 4DCBCT technique can ultimately enhance the target localization accuracy [16-18], especially for high precision treatments such as lung stereotactic body radiation therapy (SBRT) [19-21].

In 4DCBCT, all acquired X-ray projections are first grouped into different respiratory phase bins according to breathing signal amplitude tagged on the images. The CBCT image for each breathing phase is then reconstructed independently. The reconstructed 3DCBCT images for each phase are finally consolidated into a 4DCBCT image set.

Unfortunately, such a scheme usually cannot provide a sufficient number of projections for the image reconstruction of each individual phase, which results in severe streaking artifacts, especially when the FDK reconstruction algorithm [22] is applied. One way to solve this problem is to increase the sample number of X-ray projections to a sufficient level. However, such an approach not only inevitably escalates the scanning dose to the patient by multiple folds [23-25], but it can also increase the total scan time when the tube firing rate and/or image panel update rate becomes a bottle neck for the imaging system under a high projection number request [25]. In general, compared to 3D CBCT, the image quality of commercially available 4DCBCT is severely impaired due to the insufficient amount of projection data available for each phase without increased sampling.

Some investigators [26-32] have developed other reconstruction techniques, which can be divided into two categories: 1) post-processing based [26-28] and 2) iterative reconstruction (IR) based [29-32]. Techniques in the first category enhance the 4DCBCT images by deforming a priori-reconstructed 4DCBCT images for all phases into one, and subsequently, superimposing them together. The performance of these approaches, however, largely depends on the quality of a priori-reconstructed 4DCBCT, as well as on the accuracy of the deformable image registration algorithm. The algorithm can become impractical, as the a priori-4DCBCT image provides insufficient anatomical information due to the unsatisfactory quality. The latter techniques originate from compressed sensing theory [33]. Casting the 4DCBCT reconstruction problem into a convex optimization problem with regulation constraints, these techniques typically solve the 4DCBCT image using an iterative process. During each iteration, the optimization engine is driven by evaluating back-projected results of the discrepancy between forward projections of the reconstructed 4DCBCT and the original projections of the corresponding phase. Various forms of prior knowledge, such as 3D free breathing CBCT (FB-CBCT), planning CT, and motion model [34-42], have also been incorporated into the models to improve the performance of the algorithms. Using IR-based reconstruction techniques, a better quality 4DCBCT image can be achievable without the need for increasing the projection number for the current 4DCBCT scan.

Recently, the inventors proposed an efficient IR-based 4DCBCT reconstruction framework called the motion-map constrained image reconstruction (MCIR) algorithm [43]. MCIR utilizes motion masks subjected to respiratory motion in the reconstruction space to separate moving and static portions of the volumes. The 4DCBCT images can be reconstructed by updating volumetric components that are defined by motion components using retrospectively sorted projection data, while keeping stationary components with a priori-reconstructed FB-CBCT images. Using only 3DCBCT projections, the MCIR algorithm is able to reconstruct 4DCBCT images with modest improved quality, in terms of noise and the aliasing artifact, compared with other IR-based algorithms.

SUMMARY

Some aspects include a system for constructing a plurality of images representing a four-dimensional computed tomography sequence of an object from a plurality of projections. The projections may be taken from a plurality of angles with respect to the object and at a plurality of times. First portions of the object may be less static than second portions of the object. The system may comprise at least one processor configured to: iteratively process projections of the plurality of projections for a plurality of groups, each group comprising projections collected while the first portions of the object are in corresponding locations, with each iteration comprising: reconstructing first image portions representing the first portions of the object, the reconstructing of each first image portion of the first image portions being based on projections in a respective group of the plurality of groups; and reconstructing a second image portion, the second image portion representing the second portions of the object, based on projections in multiple groups of the plurality of groups and on the reconstructed first image portions.

Further aspects include a method for constructing a plurality of images representing a four-dimensional computed tomography sequence of an object from a plurality of projections. The projections may be taken from a plurality of angles with respect to the object and at a plurality of times. First portions of the object may be less static than second portions of the object. The method may comprise using at least one processor: iteratively processing projections of the plurality of projections for a plurality of groups, each group comprising projections collected while the first portions of the object are in corresponding locations, with each iteration comprising: reconstructing first image portions representing the first portions of the object, the reconstructing of each first image portion of the first image portions being based on projections in a respective group of the plurality of groups; and reconstructing a second image portion, the second image portion representing the second portions of the object, based on projections in multiple groups of the plurality of groups and on the reconstructed first image portions.

Additional aspects include a computer-readable storage medium encoded with executable instructions that, when executed by at least one processor, cause the at least one processor to perform a method for constructing a plurality of images representing a four-dimensional computed tomography sequence of an object from a plurality of projections. The projections may be taken from a plurality of angles with respect to the object and at a plurality of times. First portions of the object may be less static than second portions of the object. The method may comprise, using at least one processor: iteratively processing projections of the plurality of projections for a plurality of groups, each group comprising projections collected while the first portions of the object are in corresponding locations, with each iteration comprising: reconstructing first image portions representing the first portions of the object, the reconstructing of each first image portion of the first image portions being based on projections in a respective group of the plurality of groups; and reconstructing a second image portion, the second image portion representing the second portions of the object, based on projections in multiple groups of the plurality of groups and on the reconstructed first image portions.

DETAILED DESCRIPTION

The inventors have recognized and appreciated that the image quality of 4DCBCT images can be significantly improved if full projections, rather than only phase resolved projections (to which current IR-based algorithms are restricted for the reconstruction of each corresponding phase image), are utilized for each single phase reconstruction. Such an approach allows more information to be accommodated into the optimization scheme. The inventors have further recognized and appreciated that, using embodiments described herein, clinically viable 4DCBCT images may be reconstructed while requiring no more projection data and imaging dose than a typical clinical 3DCBCT scan, reducing the time required to collect image data and also reducing radiation exposure of a patient.

Figure 4:
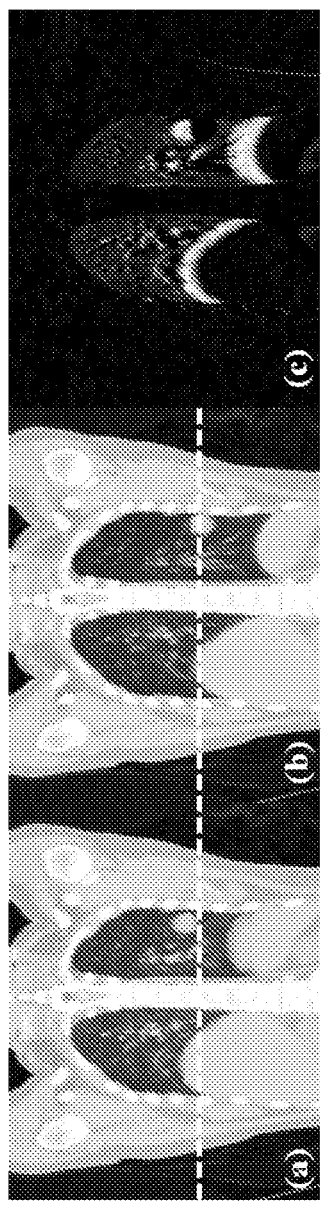
FIG. 4 is an exemplary 4DCT image of a lung cancer patient according to some embodiments.

The inventors have recognized and appreciated that for some objects, such as a human patient, not all voxels inside the 4DCBCT volume are subjected to motions (as depicted in FIG. 4). For example, when a patient is breathing, not all voxels in an image may appear to be moving. Tissues and tumors inside the lungs may move significantly along with respiratory motions, whereas tissues outside (e.g., bones, muscles, etc.) may be nearly static. Similarly, when imaging a beating heart, not all voxels may be moving. Therefore, the inventors have recognized and appreciated that whole 4DCBCT volumes can be artificially partitioned into two different kinds of volumes for, which 1) one is subjected to motion and 2) the remaining one is stationary.

The inventors have recognized and appreciated that an unknown CBCT volume may be mathematically modeled as a combination of phase-specific motion vectors and phase-independent static vectors. The inventors have further recognized and appreciated that utilizing a common-mask in the reconstruction may provide various advantages, as described herein, and may be part of a 4DCBCT reconstruction framework, described herein as common-mask guided image reconstruction (c-MGIR). A common-mask matrix may distinguish the moving voxels from the stationary ones. The moving part and the static part may be alternatively updated by solving two sub-minimization problems iteratively. As both of the sub-problems may contain the direct information of global projections as well as a "good" solution acquired from previous iteration, which may also be obtained with global projection information, the algorithm may be able to mitigate the under-sampling artifact (an issue faced by other algorithms) to a maximum extent.

The inventors have recognized and appreciated that unlike the "motion mask" concept of the MCIR algorithm, a common-mask may allow the full projection information to be used for each phase reconstruction at each optimization iteration to achieve high quality 4DCBCT images from highly under-sampled, phase resolved cone-beam projections. In particular, common-mask may separate the moving part (which may be different between phases) of the image from the static part (which may be identical among all phases) using prior 3D FB-CBCT reconstructed images. Then, some embodiments may alternatively update the moving part and the static part of the image by solving minimization problems using phase-resolved and global projection data sets, respectively. Some embodiments may be implemented with a graphics processing unit (GPU) in order to achieve a fast reconstruction time, which may help make the algorithm potentially useful in an online image-guided radiation therapy environment.

Exemplary Implementation of the System

Figure 1:
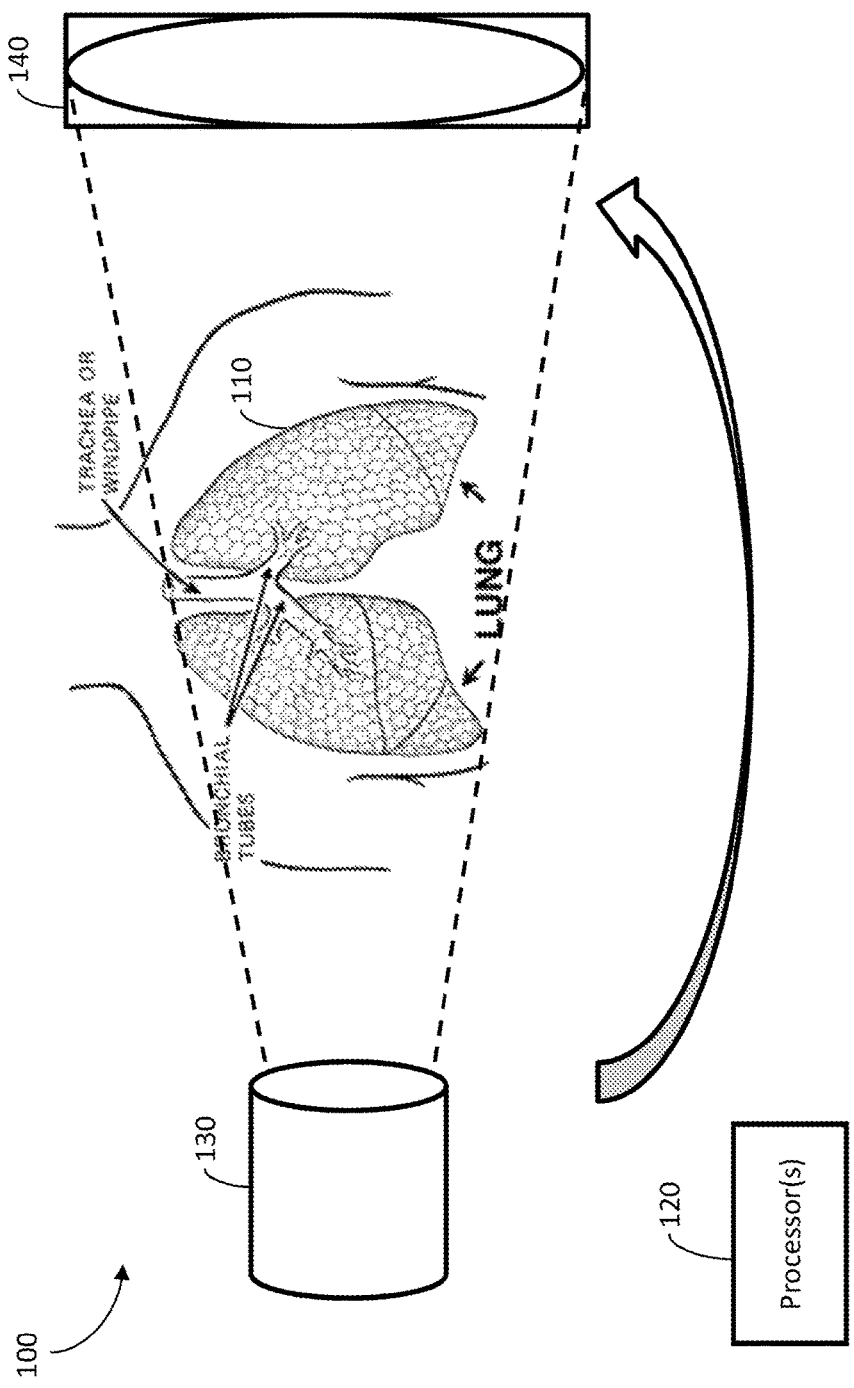
FIG. 1 is a diagram illustrating a system and environment for image reconstruction according to some embodiments.

FIG. 1 illustrates an exemplary system and environment 100 for constructing images representing a four-dimensional computed tomography sequence of an object 110. The images may be constructed or reconstructed from projections taken from multiple angles with respect to the object 110 and at multiple times (which may correspond to phases, as described herein). For example, the object 110 may be an organ, a tumor, some other portion of an organism, or any other suitable subject of CBCT scanning. Additionally, the four-dimensional computed tomography sequence may be a four-dimensional cone-beam computed tomography sequence.

According to some embodiments, some portions (which may correspond to moving portions) of the object 110 may be less static in terms of their position than other portions (which may correspond to static or stationary portions) of the object 110. For example, moving portions of the object 110, which may be a lung or lungs, may move when the patient having the lung(s) inhales or exhales, at least relative to the static portions.

According to some embodiments, the cycle of breathing may be grouped into various breathing phases or groups, as described herein. For example, FIG. 4 illustrates exemplary breathing phases (a) peak inhale 0% phase and (b) exhale 50% phase, as well as (c) the absolute difference between the two images. Using the dotted white line and (c) as references, the lung tumor inside the right lobe may exhibit significant motion, while the bones and surrounding muscle tissues may be relatively stationary.

According to some embodiments, the system and environment 100 may include one or more processors 120 coupled to an imaging system. The imaging system may collect projection data, which may be processed to form images as described herein. The system and environment 100 may also include a source 130 and a detector 140. The source 130 may emit x-rays or any other suitable radiation, which the detector 140 may detect after the emission passes through the object 110 and/or any other impediment. The source 130 and the detector 140 may be attached to a gantry for rotation around the object 110 in order to take the projections.

According to some embodiments, the processor(s) 120 may iteratively process projections for multiple groups of projections. Each group may include projections collected while the moving portions of the object are in corresponding locations. Additionally, each group may correspond to a location of the moving portions and/or one or more times. For example, the location of the moving portions for a first group may be at peak inhale 0%, and the time or times for that first group may be when the peak inhale 0% phase occurs, while the location of the moving portions for a second group may be at exhale 50%, and the time or times for that second group may be when the exhale 50% phase occurs. Such groups may be formed in any suitable way, including using techniques as known in the art for forming 4DCBCT images.

According to some embodiments, each iteration of the iterative processing may include the processor(s) 120 reconstructing first image portions representing first portions of the object 110. The reconstructing of each first image portion may be based on projections in a respective group.

Each iteration may also include the processor(s) 120 reconstructing a second image portion representing the second portions of the object 110. Additionally, the reconstructing may be based on projections in multiple groups and on the reconstructed first image portions. Because the second image portion represents stationary portions of the object, the portion of the object represented in each of the groups, even though corresponding to different phases of motion of the object, should be the same. Accordingly, combining images across multiple phases provides more data usable for image reconstruction in a shorter time.

According to some embodiments, the first image portions may include multiple motion components of the images, and the second image portion may include one or more static components of the images. Alternatively or additionally, the one or more static components of the projections may include a common static component of the images. For example, if all the projections have essentially identical static components, a single static component may be used.

According to some embodiments, reconstructing the first image portions may be based on a previous solution of reconstructing the second image portion for at least one iteration. Though each phase may be processed separately, using data for the stationary portion can increase the amount of data available for reconstructing each phase, reducing the need for more projections to be collected for each phase. For example, reconstructing the first image portions and reconstructing the second image portion may be alternated by the processor(s) 120 such that a solution or result of reconstructing of either the first image portions or the second image portion may be used by the processor(s) 120 in reconstructing the other image portions or portion. Alternatively or additionally, about 60 iterations or less of processing the projections may be performed by the processor(s) 120.

According to some embodiments, the processor(s) 120 may compute a common-mask based on differences between a 3DCBCT volume and a 4DCBCT volume, as described herein. Additionally, the processor(s) 120 may apply the common-mask to obtain an initial solution of reconstructing the first image portions and an initial solution of reconstructing the second image portion. The processor(s) 120 may use either, both, or neither of these initial solutions to increase the performance of the image reconstruction by providing an acceptable starting point for the reconstruction(s).

According to some embodiments, for each group, the processor(s) 120 may combine a solution of reconstructing the first image portions with a solution of reconstructing the second image portion. This combination may produce a constructed image for the group. For example, the constructed image may be the complete image for the corresponding phase, including both the static and motion portions. Additionally, the processor(s) 120 may combine each constructed image for each group, which may produce a series of constructed images. This series of constructed images may be a 4DCBCT series of images, which may be played back to show the locations and time-based movements of the object 110 and/or used to target the object 110 or some portion of it for radiation therapy.

According to some embodiments, the processor(s) 120 may include one or more graphics processing units. The graphics processing unit(s) may perform reconstructing the first image portions in parallel with reconstructing the second image portion and/or reconstructing the first image portions using data in multiple groups in parallel. This parallel processing may provide significant performance advantages, which may allow some embodiments to be used for "online" reconstruction and localization (e.g., the reconstruction could be performed nearly in real-time, such as within a few minutes).

Figure 2:
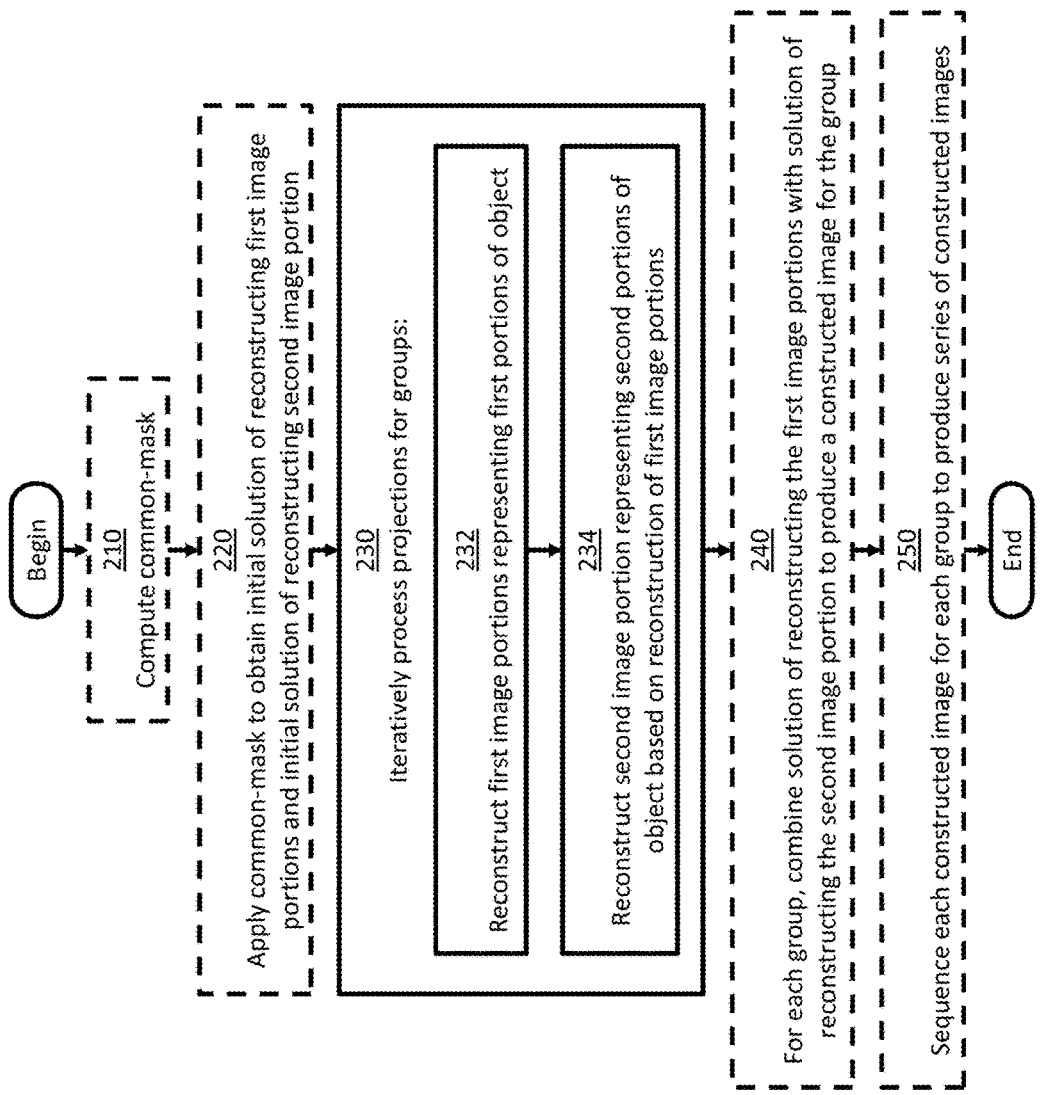
FIG. 2 is a flowchart of a method for image reconstruction according to some embodiments.

It should be appreciated from the foregoing that some embodiments are directed to a method for constructing images representing a four-dimensional computed tomography sequence of an object from projections, as illustrated in FIG. 2. The method optionally begins at act 210, at which a common-mask may be computed based on differences between a 3DCBCT volume and a 4DCBCT volume. Act 210 may include reconstructing the 3DCBCT volume based on projections collected from a CBCT system. For example, the 3DCBCT volume may be reconstructed using the FDK algorithm. Act 210 may also include updating the 3DCBCT volume for each phase of motion using phase-wise sorted projections, as described herein. For example, the 3DCBCT volume may be updated using a CS-based algorithm. This updating may produce the 4DCBCT volume. Act 210 may further include computing and summing the differences between the 3DCBCT volume and the 4DCBCT volume to obtain a normalized motion-map matrix, which may be used to calculate the common-mask, as described herein.

The method then optionally proceeds to act 220, at which the common-mask may be applied to obtain an initial solution of reconstructing the first image portions and an initial solution of reconstructing the second image portion, as described herein. Act 220 may include separating or classifying portions of the 4DCBCT volume into moving portions and static portions.

The method then proceeds to act 230, at which projections for the multiple groups may be iteratively processed. Iteratively processing the projections for the multiple groups may include acts 232 and 234 for each iteration. At act 232, the first image portions may be reconstructed using projection data for the phase of motion corresponding to each respective first image portion. At act 234, the second image portion may be reconstructed using, in addition to projection data for multiple or all phases, the reconstruction of the first image portions, as described herein.

The method then optionally proceeds to act 240, at which a solution of reconstructing the first image portions may be combined with a solution of reconstructing the second image portion for each group, producing a constructed image for the group. Optionally, the method then proceeds to act 250, at which each constructed image for each group may be combined to produce a series of constructed images, as described herein.

The method may then end. However, treatment of the person or other organism may continue as is known in the art. After the reconstruction of all the desired images is completed, for example, the images may be used to localize a tumor in time so that image-guided radiation therapy may be applied to treat it, as is known in the art.

Exemplary Methods and Materials

Separation of CBCT Images

As described above, whole 4DCBCT volumes can be artificially partitioned into two different kinds of volumes for, which 1) one is subjected to respiratory motion and 2) the remaining one is stationary. Mathematically, the relationship between a moving volume and a static volume can be described as follows.

Let $x_i$ denote the 4DCBCT image volume of i-th phase. Then, each 3D image $x_i$ can be separated into two parts: a moving part $m_i$ and a static part $s_i$, with the size m×n×k for all phase, where m, n and k defined the number of voxels of the 3D images in the Left-Right (LR), Anterior-Posterior (AP) and Superior-Inferior (SI) directions, respectively. Then the unknown image volume of i-th phase can be formulated as:

$$x_i = m_i + s_i \text{ for } i=1,\ldots,p, \text{ and } x_i, m_i, s_i \in \Re^{m \times n \times k} \quad (1)$$

where p is the total number of phases.

Furthermore, to control this separation, we let U represent the common-mask of the motion, which may be defined as $$U(x, y, z) = \begin{cases} 1, & \text{motion voxel} \\ 0, & \text{static voxel} \end{cases} U \in \{0,1\}^{m \times n \times k} \quad (2)$$

for any (x, y, z) voxel in the Cartesian coordination system. Then $x_i$ can also be expressed as $$x_i = U \cdot x_i + (1-U) \cdot x_i \text{ for } i=1,\ldots,p, \text{ and } x_i, m_i, s_i \in \Re^{m \times n \times k} \quad (3)$$

where 1 is the matrix of ones with same size as U. It should be noticed that the product terms (e.g. $U \cdot x_i$ and $(1-U) \cdot x_i$) in equation (3) represent the component-wise production between two matrices.

Since we intend to solve the motion term and the static term separately, we can rewrite equation (3) into the following form for the optimizations.

$$x_i = U \cdot m_i + (1-U) \cdot s_i \text{ for } i=1,\ldots,p, \text{ and } x_i, m_i, s_i \in \Re^{m \times n \times k} \quad (4)$$

In addition, since the static volume for all phases may be the common one, we can further rewrite Equation (4) by introducing a common static part for all phases denoted by s, and obtain the following separation of the 4DCBCT images:

$$x_i = U \cdot m_i + (1-U) \cdot s \text{ for } i=1,\ldots,p, \text{ and } x_i, m_i, s_i \in \Re^{m \times n \times k} \quad (5)$$

where $Um_i$ and $(1-U)s$ represent the possible motion part and the common static part in $x_i$, respectively.

c-MGIR Algorithm

As was mentioned above, the limited number of projections available for each phase reconstruction may be the largest obstacle to achieving good image quality. Therefore, it may be crucial to provide an optimization scheme to overcome this intrinsic difficulty. The following context describes how some embodiments resolve this under-sampling issue in detail.

According to some embodiments, the 4DCBCT images may be obtained by solving the following constrained convex optimization problem:

$$\min_{m_i, s} \frac{1}{2} \sum_{i=1}^{P} \|A_i(U \cdot m_i + (1-U) \cdot s) - b_i\|_F^2 + \lambda_1 TV(U \cdot m_i) + \lambda_2 TV((1-U) \cdot s) \text{ s.t. } m_i, s \geq 0 \quad (6)$$

where $b_i \in R^{l \times q \times v}$ is defined as the sorted projection data for phase i, for which l×q and v represent the 2D projection size and full projection number respectively; $A_i$ is defined as the Radon transform operator $A_i: R^{m \times n \times k} \to R^{l \times q \times v}$ for the i-th phase which can transform the volume of i-th phase to the sorted projections of the same phase; λ1 and λ2 denote regularization term constants for the moving and stationary volumes respectively; and TV denotes the Total Variation (TV) regularization term.

In equation (6), $\|\cdot\|_F$ is the Frobenius norm, and the TV term used in this study may be defined as $$TV(x) = \sum_{i,j,k} \left( \sqrt{\begin{array}{c}(x(x+1,y,z)-x(x,y,z))^2 + \\ (x(x,y+1,z)-x(x,y,z))^2 + \\ (x(x,y,z+1)-x(x,y,z))^2\end{array}} \right) \quad (7)$$

Unlike the regular CS type optimization formulation, in Equation (6), the 4DCBCT volume may be split to two variables according to Equation (5); a static component, s, and a moving component, $m_i$, for each phase. The TV terms may also be split into two terms to accommodate their corresponding fidelity term. This new formulation can promote the sparseness of attenuation variation characteristics for both the moving and stationary parts of the human anatomy. Assuming that the common-mask U is known, which will be discussed below, Equation (6) can be solved by alternatively updating $m_i$ and s using the following sub-optimization formulas:

$$s^{k+1} = \underset{s}{\text{argmin}} \frac{1}{2} \sum_{i=1}^{p} \|A_i(U \cdot m_i^{k+1} + (1-U) \cdot s) - b_i\|_F^2 + \quad (8)$$

$$\lambda_2 TV((1-U) \cdot s) \text{ s.t. } s \geq 0$$

$$m_i^{k+1} = \underset{m_i}{\text{argmin}} \frac{1}{2} \sum_{i=1}^{p} \|A_i(U \cdot m_i + (1-U) \cdot s^k) - b_i\|_F^2 + \quad (9)$$

$$\lambda_1 TV(U \cdot m_i) \text{ s.t. } m_i \geq 0$$

To solve the sub-optimization problems above in an efficient manner, we rewrite the Equations (8) and (9) by introducing two properties to establish the matrix relationship between full projections and phase sorted projections.

First, let us denote the full projection data as $b \sqsubset R^{l \times q \times v}$. Here, it should be noted that the projection data of i-th phase $b_i$ may have the same size as the full projection data b. Moreover, the non-zero entry of matrix $b_i$ may be a sub set of matrix b. In other words, $b_i$ may be the matrix b for which some entries were set to $0 \in R^{l \times q}$ if the corresponding projections were not included in the data set of i-th phase. Thus, we have the following property:

Property 1.

The sum of partial projection data $b_i$ is equal to the full projection data b, that is $$\sum_{i=1}^{p} b_i = b \quad (10)$$

Likewise, we defined the radon transform operator for full projections as A: $R^{m \times n \times k} \rightarrow R^{q \times l \times v}$, the linear projection operator mapping the object images to all available projections. Deriving from property 1, we can arrive at the following property:

Property 2.

The sum of partial projection radon transform operation is equivalent to the full projection radon transform operation, that is $$\sum_{i=1}^{p} A_i(x) = A(x) \quad (11)$$

Following property 1, property 2 and the definition of $A_i$ and $b_i$, we can conclude that among the same entry location of the matric serial: $A_i (U \cdot m_i^{k+1} + (1-U)s) - b_i$ for i=1, ..., p; at most one entry possesses a non-zero value. Thus, focusing on the first term on the right hand side of equation (8), we have $$\sum_{i=1}^{p} \|A_i(U \cdot m_i^{k+1} + (1-U)s) - b_i\|_F^2 = \quad (12)$$

$$\left\| \sum_{i=1}^{p} (A_i(U \cdot m_i^{k+1} + (1-U) \cdot s) - b_i) \right\|_F^2 =$$

$$\left\| \sum_{i=1}^{p} A_i(U \cdot m_i^{k+1}) + \sum_{i=1}^{p} A_i((1-U) \cdot s) - \sum_{i=1}^{p} b_i \right\|_F^2 =$$

$$\left\| A((1-U) \cdot s) + \sum_{i=1}^{p} A_i(U \cdot m_i^{k+1}) - b \right\|_F^2 = \left\| A((1-U) \cdot s) - \hat{b} \right\|_F^2$$

Where $$\hat{b} = b - \sum_{i=1}^{p} (A_i(U \cdot m_i^{k+1})) \quad (13)$$

For equation (9), we also define:

$$\hat{b}_i = b_i - (1-U) \cdot s^k \quad (14)$$

for the sake of simplicity.

Finally, equations (8) and (9) are rewritten as follows $$m_i^{k+1} = \underset{m_i}{\text{argmin}} \frac{1}{2} \|A_i((U \cdot m_i) - \hat{b}_i)\|_F^2 + \lambda_1 TV(U \cdot m_i) \text{ for all } i, \quad (15)$$

$$i = 1 \ldots p; \text{ s.t. } m_i \geq 0$$

$$s^{k+1} = \underset{s}{\text{argmin}} \frac{1}{2} \|A((1-U) \cdot s) - \hat{b}\|_F^2 + \lambda_2 TV(1-U) \cdot s) \quad (16)$$

$$\text{s.t. } s \geq 0$$

To solve the sub-optimization problems in equations (15) and (16) numerically, the gradient descent algorithm with the Barzilai-Borwen (BB) setup size [44-45] has been adopted. The principle of this algorithm has been described in our previous studies [43, 47] and will not be repeated here. Below we describe how the BB method was implemented for some embodiments in a detailed mathematical form.

Here, the main features of some embodiments can be summarized two folds. 1. Compared to other algorithms, the some embodiments of the c-MGIR may break down the original p linear systems and reform them into p smaller sized linear systems (respect to $m_i$) and one larger sized linear system (with respect to s). 2. The new form of the problem may allow some embodiments of the algorithm to utilize full projection data for each iteration process, which may fundamentally overcome the under-sampling issue faced by other CS based algorithms. More specifically, the full projection data b, has been used in equation (15) to obtain the solution s, and subsequently, equation (16) can take advantage of the "well" solved s to acquire the high quality $m_i$.

Common-Mask Calculation

Acquiring the common mask U may be the first step and a critical step for the some embodiments of the c-MGIR algorithm. The effectiveness of some embodiments of the c-MGIR algorithm may be largely dependent upon how well the common-mask, which separates moving and stationary components of the images, can be identified. To obtain the common-mask U, we used $x_i$ volumes extracted from the computing process of U as our initial solution to start the optimization on equations (15) and (16) rather than maneuver the U calculation and optimization iterations as two completely separate steps, as MCIR did. In this way, some embodiments of the entire algorithm can become more computationally effective. The common mask calculation method can be briefly described as follows.

The common-mask may be extracted from the normalized difference map between the 3D-CBCT volume, $x_{3D}$, reconstructed using full projection, and the 4DCBCT phase volume, $x_i$, reconstructed using phase sorted projections. $x_{3D}$ can be quickly obtained through the regular FDK algorithm. To solve $x_i$, we use the following optimization form:

$$x_i^k = \underset{x}{\mathrm{argmin}} \frac{1}{2}\|A_i(x_i) - b_i\|_F^2 + \lambda_3 TV(x_i) \text{ s.t. } x_i \geq 0 \quad (17)$$

The optimization process is initialized by setting $x_i^0 = x_{3D}$, and the same BB gradient method is employed to obtain the solutions after the k-th iteration (k=10 in our study). Then the motion map can be calculated using the following normalization form:

$$M(x, y, z) = \frac{\hat{M}(x, y, z) - \min_{x,y,z} \hat{M}(x, y, z)}{\max_{x,y,z} \hat{M}(x, y, z) - \min_{x,y,z} \hat{M}(x, y, z)} \quad (18)$$

where $$\hat{M}(x, y, z) = \sum_{i=1}^{P} |x_{3D}(x, y, z) - x_i^k(x, y, z)| \quad (19)$$

Finally, the common-mask U may be computed by classifying all of the voxels into two types (stationary and moving components) with threshold T of M. That is:

$$U(x, y, z) = \begin{cases} 1, & \text{if } M(x, y, z) \geq T \\ 0, & \text{otherwise} \end{cases} \quad (20)$$

Once the common-mask U is computed, it can be applied to the solution, $x_i$, of equation (17) to obtain the initial $m_i$ and s to start the optimization process of equation (15) and (16). In this manner, the whole process of reconstruction can be much more efficient because the initial solution is already a good one.

c-MGIR Practical Implementation Using GPU

The pseudo-code of c-MGIR algorithm has been laid out below. Some embodiments of the c-MGIR algorithm use an iterative optimization process, which may be computationally heavy. It can take hours of CPU time to reach a solution, which may be inadequate for an online reconstruction algorithm. To significantly improve the algorithm speed, parallelized code may be used with the GPU (NVIDIA GTX 780Ti, Santa Clara, Calif.) in the CUDA C/C++ programming environment. Major computational tasks such as forward projection, back projection, and vector operations may be efficiently parallelized by the GPU code. Interested readers can refer to our previous study [46] for a description of the GPU implementation.

Exemplary Comparisons Between c-MGIR and other Algorithms using the Phantom and the Patient Data To evaluate the performance of the some embodiments of c-MGIR, data for both a numerical phantom and a lung cancer patient were analyzed. The numerical phantom is a dynamic chest phantom that simulates respiratory motion by expanding, shrinking, and/or laterally moving two circular objects located inside the chest wall of the phantom. A five seconds cycle was set for the phantom breathing motion with a cosine function for the motion amplitude. Six hundred simulated projections were acquired in a virtual full-gantry rotation. The projections were then sorted into 40 phases, which resulted in 15 projections available for each phase reconstruction. Five different algorithms were used for the image reconstructions. They were: 1) the FDK algorithm, 2) the Conventional Total Variation (CTV) Algorithm; and 3) the Prior Image Constrained Compressed Sensing (PICCS) algorithm, 4) the MCIR algorithm and 5) some embodiments of the c-MGIR algorithm. For fair comparisons, 200 equivalent iterations were run for phantom reconstructions for all algorithms using the same BB step-size optimization approach. Line profiles of both the static and moving components of the numerical phantom were compared between the ground truth volume and the volumes reconstructed by all of the algorithms. The root mean square errors (RMSE) from the ground truth were also compared with those from all of the algorithms. The RMSE is defined as:

$$RMSE(\%) = \sqrt{\frac{\sum_{x,y,z}(x_{x,y,z} - x_{x,y,z}^{Ground\,Truth})^2}{\sum_{x,y,z}(x_{x,y,z}^{Ground\,Truth})^2}} \times 100 \quad (21)$$

where $x_{i,j,k}$ corresponds to the voxel values in the reconstructed volume, x, and $x^{Ground\,Truth}$ refers to the ground truth values of the phantom. Finally, we have compared the convergence rate of all iterative algorithms (CTV, PICCS, MCIR, and some embodiments of c-MGIR) as a function of RMSE.

For the clinical lung cancer case, the patient's CBCT projections were obtained from the X-ray Volumetric Imaging (XVI™, Elekta Oncology Systems Ltd, Crawley, UK) system. The imager has 1024×1024 pixels with a 0.4×0.4 mm² resolution. This resolution was down-sampled to 512×512 pixels with a 0.8×0 8 mm² for the reconstruction using 2 by 2 binning process. A two minutes FB-CBCT scan and a four minute 4D-CBCT scan were acquired for this patient with 670 projections and 1257 projections available for the reconstructions respectively. During the acquisition, each projection was tagged with the phase information using Amsterdam Shroud approach. Then, the projections were retrospectively sorted into 10 different phases. All 4DCBCT volumes were reconstructed with 256×256×70 voxels at a resolution level of 1.8×1.8×2.5 mm³ The image quality comparison of the 4D-CBCTs took place among the 4D volumes reconstructed by FDK with 4D-CBCT scan projections (1257), FDK with FB-CBCT scan projections (670), MCIR with FB-CBCT scan projections, and some embodiments of c-MGIR with FB-CBCT scan projections. Total 61 equivalent iterations were used as the stopping criteria for some embodiments of c-MGIR and MCIR algorithms. Eventually, the computation times of some embodiments of c-MGIR and other algorithms were also listed.

Exemplary Results

Figure 5:
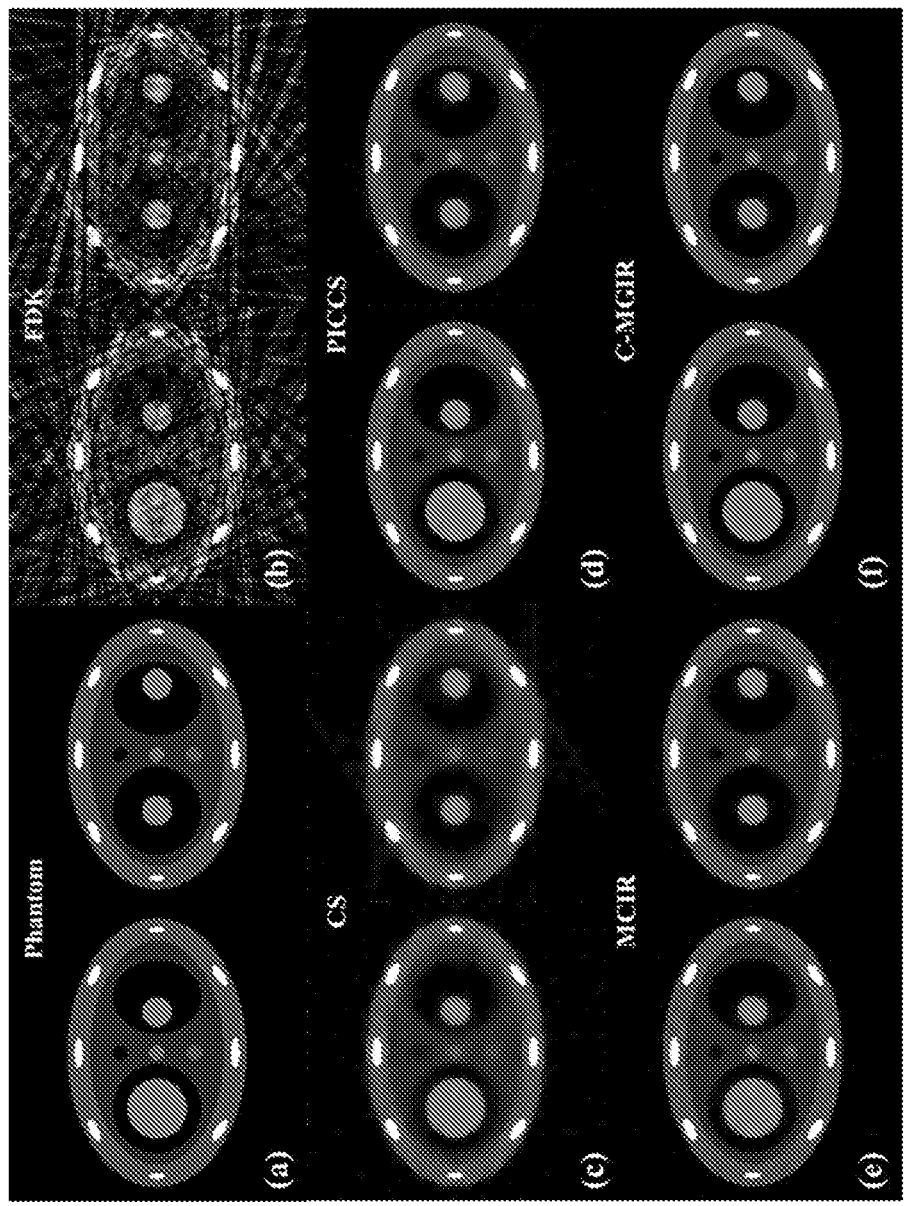
FIG. 5 is an illustration of exemplary numerical 4D phantom simulation results according to some embodiments.

FIG. 5 shows axial images for the numerical phantom as well as the same axial slices at both the 0% phase and the 50% phase reconstructed using the FDK, CTV, PICCS, MCIR, and some embodiments of c-MGIR respectively. More specifically, FIG. 5 shows (a) a ground truth phantom image at two phases 0% and 50%, (b) a 4DCBCT image reconstructed using FDK, (c) a 4DCBCT image reconstructed using the CS, (d) a 4DCBCT image reconstructed using the PICCS, (d) a 4DCBCT image reconstructed using the MCIR, and (f) a 4DCBCT image reconstructed according to some embodiments. Severe streaking artifacts appeared in the image reconstructed using the FDK algorithm (FIG. 5(b)). Some of the structures in the medial aspect of the phantom are nearly indistinguishable due to these artifacts. The CTV algorithm (FIG. 5(c)), however, reduces the streak artifacts significantly. Even so, some medial structures still possess the blurring appearance. As for the PICCS (FIG. 5(d)) and MCIR (FIG. 5(e)) they show significantly improved image quality as compared to the CTV. However, patching artifacts on the static background structures were still noticeable. By contrast, some embodiments of the c-MGIR algorithm (FIG. 5(f)) may have almost no visible artifact and the level of agreement with the ground truth images (FIG. 2(a)) may be closest compared to the other algorithms. Magnified images of FIG. 5 are shown in FIG. 6 for a more detailed analysis.

Figure 6:
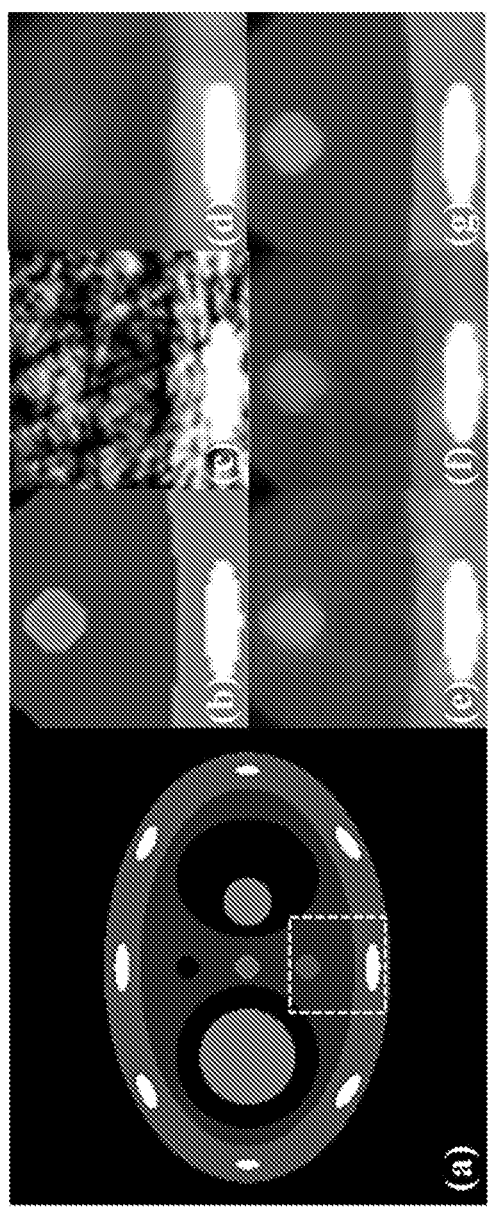
FIG. 6 is a magnified illustration of exemplary numerical 4D phantom simulation results according to some embodiments.

FIG. 6 shows a magnified region of interest at a static component of a 4D phantom at 0% phase, (a) a numerical phantom representing the region of interest (dotted box), (b) a ground truth phantom, (c) a 4DCBCT image reconstructed using FDK, (d) a 4DCBCT image reconstructed using the CS, (e) a 4DCBCT image reconstructed using the PICCS, (f) a 4DCBCT image reconstructed using the MCIR, and (g) a 4DCBCT image reconstructed according to some embodiments.

Figure 7:
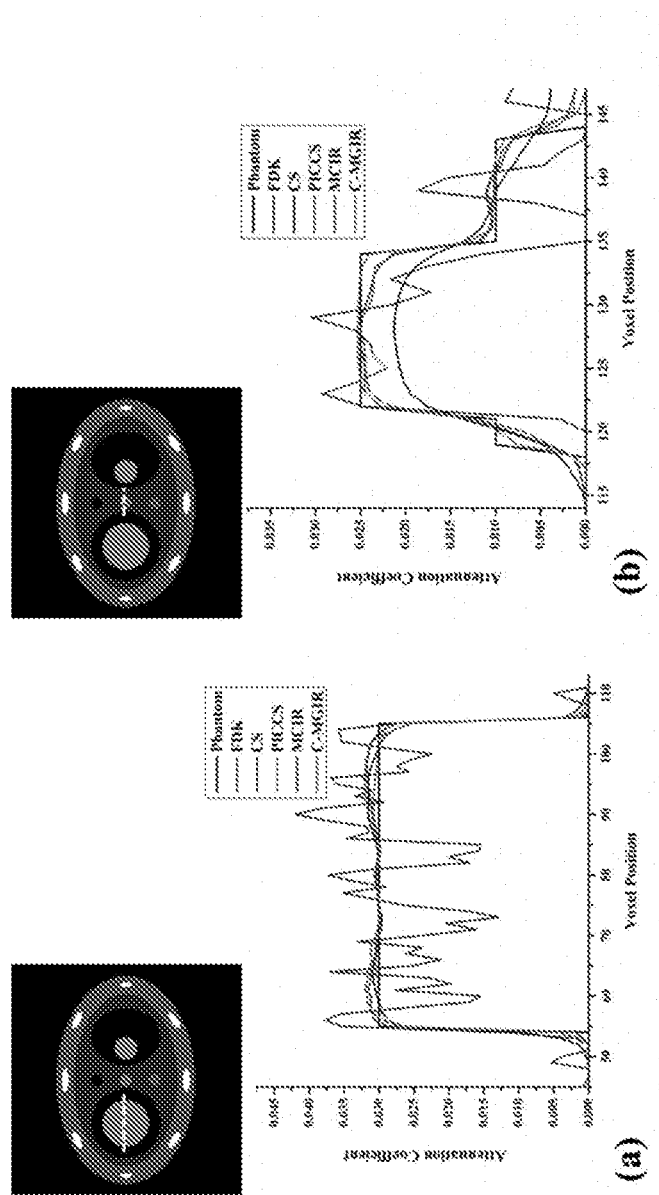
FIG. 7 is an illustration of exemplary measured line profiles of (a) a moving object and (b) a static object in the 0% phase numerical phantom according to some embodiments.

The profiles crossing both moving and static parts are displayed in FIG. 7. FIG. 7 illustrates that some embodiments of the c-MGIR algorithm may lie closest to the ground truth phantom profile.

Figure 8:
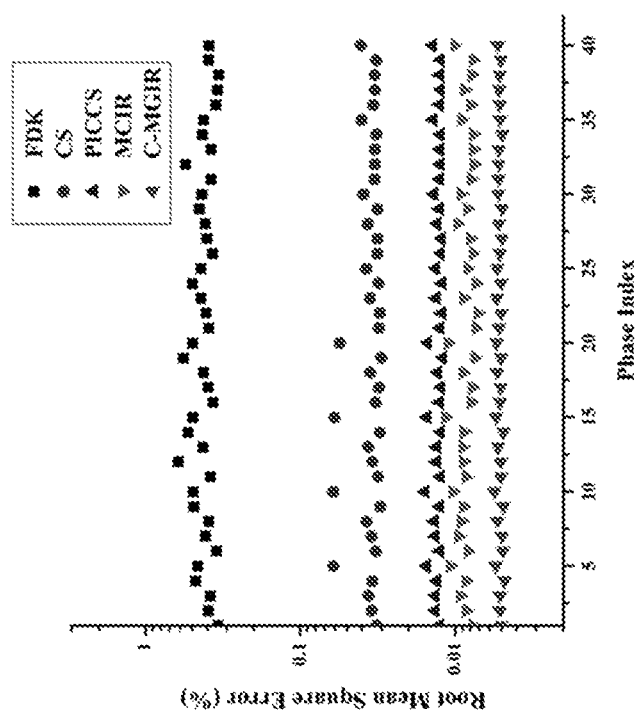
FIG. 8 is an illustration of exemplary results comparing the root mean square errors between 4DCBCT images reconstructed using the FDK, CS, PICCS, MCIR, and some embodiments across 40 phase images.

FIG. 8 illustrates the calculated RMSE for all 40 phase images. It demonstrated that the level of agreement with the ground truth is, in descending order: c-MGIR, MCIR, PICCS, CTV, and FDK for all phases. Moreover, some embodiments of c-MGIR also possess the best consistency of RMSEs among all phases compared to the other algorithms.

RMSE between the ground truth and reconstructed volumes of the numerical phantom were in the descending order of FDK, CTV, PICCS, MCIR, and some embodiments of c-MGIR for all phases. Specifically, the means and the standard deviations of the RMSE of FDK, CTV, PICCS, MCIR, and some embodiments of c-MGIR for all phases were 42.64±6.5%, 3.63±0.83%, 1.31%±0.09%, 0.86%±0.11%, and 0.52%±0.02% respectively.

Figure 9:
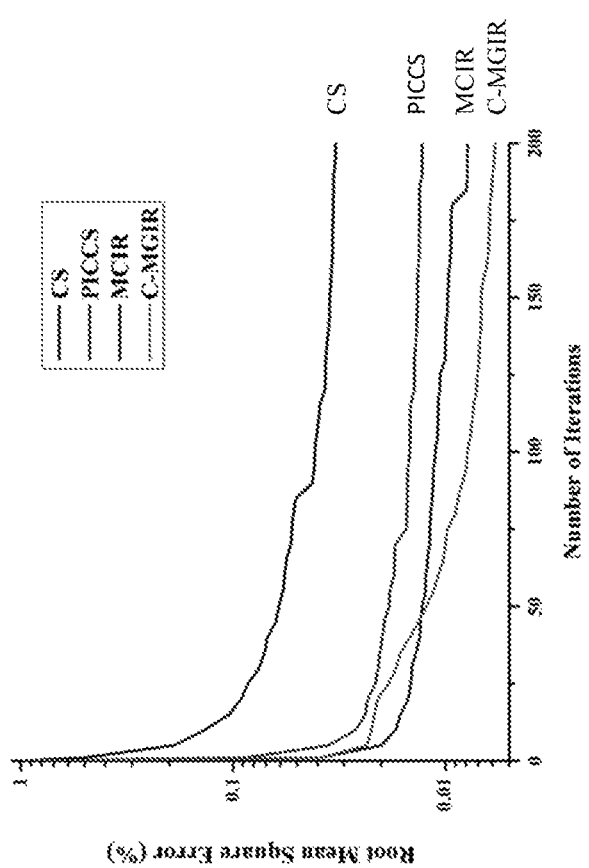
FIG. 9 is an illustration of exemplary results comparing the variation of root mean square errors calculated over each iterative step during the 4DCBCT reconstruction of a 0% phase numerical phantom for the CS, PICCS, MCIR, and some embodiments.

FIG. 9 shows the convergence as a function of RMSE for all algorithms. The RMSE for some embodiments of c-MGIR was measured after each inner iterative loop to present a fair comparison. Note that FDK is excluded from the comparison because it is not an iterative reconstruction algorithm.

Some embodiments the of c-MGIR algorithm may need less than 60 iterations to achieve less than 1% RMSE value from the ground truth, whereas the CTV, PICCS, and MCIR need more iterations to reach the same level of image quality, which indicates that some embodiments of c-MGIR out-performed the other algorithms in terms of the overall time to reach the optimum solution. It is also of note that the initial convergence rate of some embodiments of the c-MGIR algorithm is slightly slower than for the MCIR algorithm, within 50 iterations. However, after 20 iterations, the speed of the RMSE fall-off, while some embodiments of the c-MGIR algorithm accelerated dramatically, being much faster than any of the algorithms listed.

Figure 10:
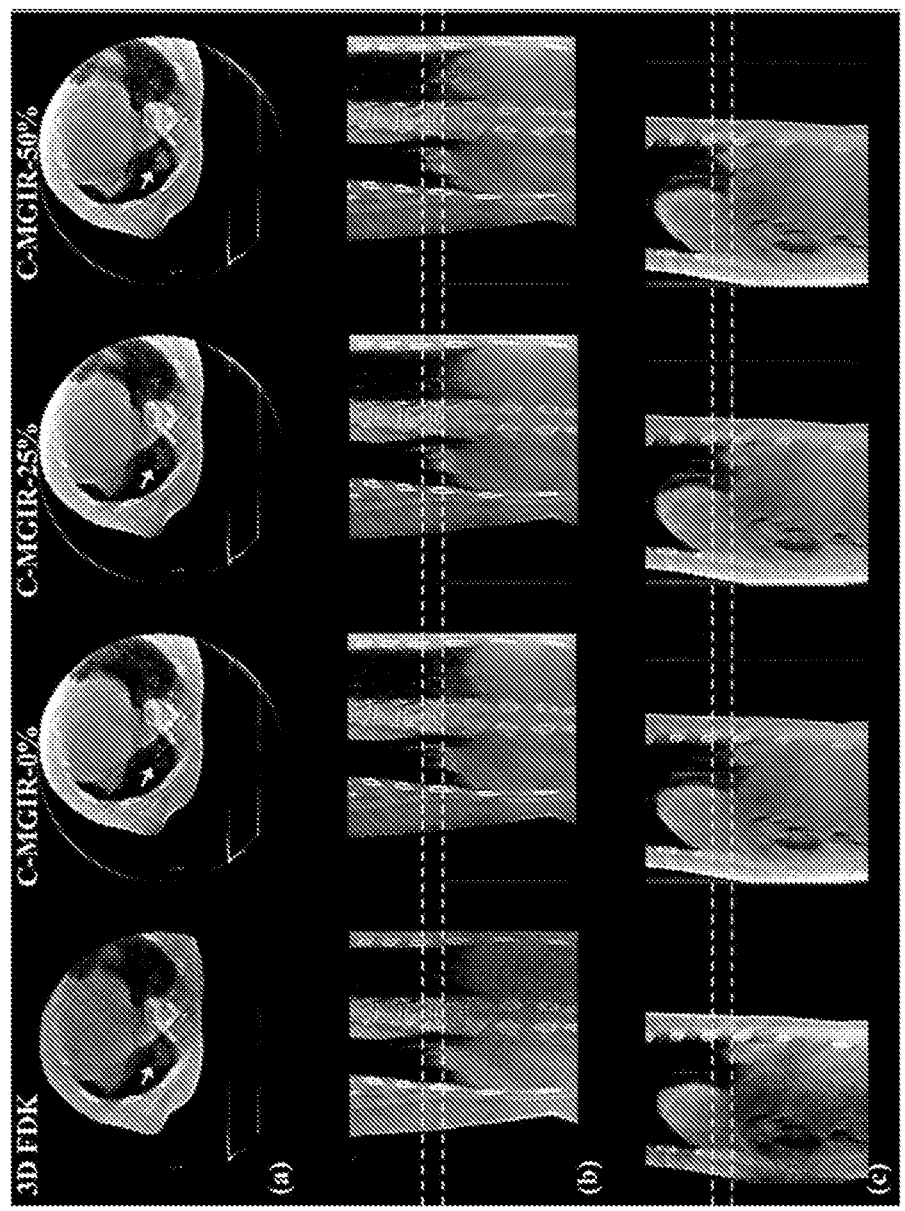
FIG. 10 is an illustration of (a) Axial, (b) Coronal, and (c) Sagittal images of a lung cancer patient comparing algorithms with some embodiments.

FIG. 10 shows the lung cancer patient's axial, coronal, and sagittal images, which were reconstructed by FDK with the FB-CBCT projections as well as by some embodiments of the c-MGIR algorithm with sorted 4D-CBCT projections at 0% phase (peak-exhale), 20% phase (mid-inhale), and 50% phase (peak-inhale). Regarding soft tissue (e.g. liver) noise, and hard tissue (e.g. ribs) contrast as well as diaphragm position distinction, the 4D phase images reconstructed by some embodiments of the c-MGIR algorithm outperformed the FB-3DCBCT reconstructed with FDK. FIG. 10 illustrates FB-3DCBCT in the first column and the c-MGIR algorithm at 0% phase in the second column, 25% phase in the third column, and 50% phase in the fourth column. The image quality of some embodiments of the c-MGIR algorithm for all phases is superior to that of FB-3DCBCT on both soft and hard tissues.

Figure 11:
FIG. 11 is an illustration of (a) axial and (b) coronal cut of a 0% phase lung cancer patient comparing algorithms with some embodiments.

FIG. 11 displays the 0% 4DCBCT images reconstructed by the FDK algorithm with 4DCBCT projections (1257 projections) in the first column, and the MCIR in the second column and some embodiments of the c-MGIR algorithm in the third column with FB-3DCBCT projections (670 projections). Despite the fact that about twice as many projections are being used compared with the other two algorithms, severe streaking artifacts still exist in the 4D-FDK. By contrast, no severe streaking artifact was present in the images reconstructed by both MCIR and some embodiments of c-MGIR. FIG. 11 also demonstrates that soft tissue noise and streak artifact has been further reduced and hard tissue contrast has been further enhanced by the c-MGIR algorithm as compared to the images reconstructed by the MCIR algorithm.

Finally, Table I lists the breakdown of reconstruction time achieved by some embodiments of the c-MGIR algorithm as well as the total calculation time for the 4D FDK algorithm and the MCIR algorithm. The time to reconstruct ten phase volumes of 256×256×256 voxels by c-MGIR was about 8 minutes with a single GPU implementation. MCIR used total about 7 minutes to accomplish all 10 phase calculation with the same resolution whereas FDK used about 30 second to finish the reconstruction.

TABLE I

Computation at each iterative stage and total reconstruction time for some embodiments of the c-MGIR.

| Processing Type | Time/Iteration (sec) | # Iterations | Total Time (sec) |
| --- | --- | --- | --- |
| Common-mask Calculation (Eq. 18) | 7.49 | 5 | 37.46 |
| Inner Iterative Loop #1 (Eq. 12) | 8.64 | 7 | 60.46 |
| Inner Iterative Loop #2 (Eq. 13) | 6.44 | 7 | 45.07 |

TABLE I-continued

Computation at each iterative stage and total reconstruction time for some embodiments of the c-MGIR.

| Processing Type | Time/Iteration (sec) | # Iterations | Total Time (sec) |
|---|---|---|---|
| Outer Iterative Loop #2 (Eq. 12 + Eq. 13) | 105.76 | 4 | 423.04 |
| C-MGIR | | | 469.23 |

Discussion

As described above, high quality phase resolved images can be reconstructed using clinical FB-CBCT scan projections without the need of increasing imaging dose or scanning time. Some embodiments of c-MGIR algorithm include important features, such as the following: 1. Some embodiments of c-MGIR may introduce a separable common-mask that may separate moving part of the images from the static part and solve them simultaneously with two sub-optimization problems. It should be emphasized that the strategy of solving the moving and static volumes between the MCIR algorithm and some embodiments of c-MGIR are fundamentally distinct. For example, the MCIR algorithm only updated moving anatomy at each iteration while keeping the static volume acquired from FDK reconstructed 3D FB-CBCT. In contract, some embodiments of the c-MGIR algorithm may update both moving and static volumes with two separable fidelity terms and two separable energy terms. 2. With the global optimization scheme, full projection information may be utilized by some embodiments of c-MGIR for every iteration process to update both moving and static volumes, which may fundamentally overcome the under-sampling issue faced by other CS-based algorithms.

Among all steps of c-MGIR, common-mask estimation may be the first step as well as a vital step that can profoundly influence the performance of c-MGIR algorithm. The inventors have recognized and appreciated that in the MCIR algorithm, mask estimation faced two major issues: 1. Due to the unideal image quality (e.g. noise and artifacts) of a priori reconstructed FB-3DCBCT images, the resultant mask contained too many scattered small volumes which should not belong to the true mask volume. 2. The partition procedure of making the mask can create a discontinuity effect along the mask border caused by the separable reconstruction procedures on moving and static volumes. Such effect can hamper the overall image quality of the final reconstructed 4D images. To resolve the first issue, we applied volumetric median filter to the initial calculated common-mask to remove unreal small mask volumes. To resolve the image discontinuity issue, instead of using binary mask, we convolved a Gaussian kernel to the original binary mask to generate a new mask with a blurry boundary. As a result, the element values around the boundary of the binary mask may now become real numbers between 0 and 1 in the new mask rather than 0 or 1. In this way, the moving and static volumes generated by equation 3 and equation 4 may not be two totally separated volumes anymore, which were overlapped around the original boundary. As the result, the discontinuity effect along the boundary of binary mask may be removed in the final reconstructed 4D volumes.

In some embodiments of the c-MGIR algorithm, three weighting parameters may need to be assigned for the optimization: the coefficients ($\lambda_1$, $\lambda_2$) of TV regularization terms for moving and static part in equation (6) and the coefficient ($\lambda_3$) of the TV regularization term in equation (17) for mask generation purpose. In general, the higher weighting on the TV regularization terms, the blurrier and smoother images may be expected to be. In contrast, with higher weighting on the fidelity terms, sharper and noisier image may be expected. Therefore, choosing appropriate TV coefficients may be crucial for the image quality. Some studies had investigated the strategies of tuning the weighting factor of regularization terms for CBCT reconstructions and other similar optimization problems [51-54]. However, there may not be a global tactic of choosing regularization parameter for all different CBCT reconstruction applications. In our study, the coefficients of the regularization parameters were determined empirically, which may be set as $\lambda_1=2.5\times10^{-5}$ and $\lambda_2=\lambda_3=1.0\times10^{-4}$ for the lung cancer patient case.

The algorithm computational time may be another key factor to be considered, as 4DCBCT may be an online localization system and may require a reasonably fast calculation speed. In other words, the algorithm efficiency may directly impact whether some embodiments of c-MGIR can be successfully applied in the clinic scenarios. With some embodiments of c-MGIR, 8 minutes of total computation time may be needed to accomplish all steps of some embodiments of the c-MGIR algorithm for a clinical lung cancer patient case using a single GPU system. This computation time is comparable to previously reported CS based 4DCBCT reconstruction framework. With 2 minutes estimated scanning time, around 10 minutes duration is required to obtain the 4D images if some embodiments of c-MGIR are implemented into current XVI scanning system. Some embodiments may be able to operate in less time.

According to some embodiments, utilizing enhanced parallel computing strategy such as multi-GPUs can further reduce the computational time by multiple folds. Alternatively, casting c-MGIR into a more proficient optimization algorithm may improve the algorithm speed.

According to some embodiments, the common-mask concept may not be limited to dynamic image (e.g., 4DCBCT) reconstruction, but may be applied to other related image reconstruction. According to some embodiments, low dose CBCT reconstruction may utilize a common-mask to separate CBCT regions into two regions: 1) the regions where the resolution needs to be preserved, and 2) the region where streak or noise needs to be mitigated. Additionally, the two volumes can be optimized separately to obtain the overall image quality needed.

Exemplary Processing to Solve Sub-Optimization Problems Numerically

Sub-problems defined in Equation (15) and (16) may be solved using a gradient descent algorithm with Barzilai-Borwein (BB) step size [44, 45]. Specifically, we let $g_i$ and g present the gradients of the functions defined in Equation (15) and (16) respectively; and let B and $B_i$ represent the inverse Radon transfer matrix for static volume and moving volume respectively. If equation (3) and (4) was also applied, then we have, $$g_i(m_i) = U^T \cdot (B_i^T (B_i(U \cdot m_i) - \hat{b}_i)) + \lambda_1 \nabla TV(U \cdot m_i) \qquad (22)$$

$$g(s) = (1-U)^T \cdot (B^T (B((1-U) \cdot s) - \hat{b})) + \lambda_2 \nabla TV((1-U) \cdot s) \qquad (23)$$

Finally, we obtain the following updating rule for the sub-problems by setting $k_1$ and $k_2$ to be the index of each inner iteration respectively:

$$s^{k2+1} = s^{k2} - \beta^{k2} g_i(s^{k2}) \qquad (24)$$

$$m_i^{k1+1} = m_i^{k1} - \alpha_i^{k1} g_i(m_i^{k1}) \qquad (25)$$

where the BB step sizes are calculated as:

$$\alpha_i^{k1} = \langle m_i^{k1} - m_i^{k1-1}, m_i^{k1} - m_i^{k1-1}\rangle / \langle g(m_i^{k1}) - g(m_i^{k1-1}),$$
$$m_i^{k1} - m_i^{k1-1}\rangle \quad (26)$$

$$\beta^{k2} = \langle s^{k2} - s^{k2-1}, s^{k2} - s^{k2-1}\rangle / \langle g(s^{k2}) - g(s^{k2-1}), s^{k2} - s^{k2-1}\rangle \quad (27)$$

Exemplary Steps and Pseudo-code of c-MGIR Algorithm

The detailed workflow of some embodiments of the c-MGIR algorithm may be described as follows. Step 1: a priori reconstructed 3DCBCT may be reconstructed using FDK algorithm with full projections, and it may be used as the initial solution for common-mask generation. Step 2: the priori 3DCBCT volume may be updated with phase-wise sorted projections by a conventional CS-type algorithm for each phase (equation (17)). Then the updated volumes of all phases may be subtracted from the priori-3DCBCT according to equation (19). The differences may subsequently be summed to obtain normalized motion-map matrix M according to equation (18). Eventually the mask may be calculated according to equation (20) with T=0.015. Meanwhile, updated phase volumes may be obtained from equation (17) and may be used as a good initial solution for the following reconstruction process. Step 3: the static volume and moving volumes for all phases may be solved by updating two sub-optimization problems (equations (15) and (16)) alternatively. Two minimization loops corresponding to the two sub-optimization procedures are illustrated in the algorithm below (showing a computational process that may occur at each iteration for c-MGIR algorithm). In the first minimization step, the motion volumes may be updated with phase-wise sorted projections by using the motion-free volume updated from the second minimization step. In the second step, the motion-free regions may be updated using the motion volumes updated from first step. These two procedures may be iteratively repeated until updated 4DCBCT volume reaches a desired image quality.

```
Algorithm: c-MGIR-4DCBCT
```

Input: $\lambda_1, \lambda_2, U = 1$ and $x_i^0 = x_{3D}$, for $i = 1, \ldots, p$ and $b = \Sigma_{i=1}^p b_i$.
for $k = 0$ to $N$ do
   if $k \leq K$ then
      Update $x_i^k$ by solving:

$$\min_x \frac{1}{2} \| B_i x_i - b_i \|_F^2 + \lambda_1 TV(x)$$

if $k = K$ then
         1. Calculate U by Equation (19) and (20).
         2. $m_i^k = U \cdot x_i^K$ and $s^K = (1 - U) \cdot x_{3D}$.

else
      1. For $i = 1, \ldots, p$, update $m_i^{k+1}$ by solving $$\min_m \frac{1}{2} \| B_i(U \cdot m) - \hat{b}_i \|_F^2 + \lambda_1 TV(U \cdot m)$$

where $\hat{b}_i = b_i - B_i(1 - U) \cdot s^k$.
      (a) Initial $m_0 = m_i^k$ and $a_i^0$.
      (b) $m_1 = m_0 - a_i^0(U^T \cdot (B_i^T(U \cdot m_0) - \hat{b}_i)) + \lambda_1 U^T \cdot \nabla TV_c(U \cdot m_0))$.
      (c) For $n = 1, \ldots, N_1$:
         i. Calculate $g_i(m_n) = U^T \cdot (B_i^T(B_i(U \cdot m_n) - \hat{b}_i)) + \lambda_1 U^T \cdot \nabla TV_c(U \cdot m_n)$.
         ii. Calculate $a_i^n = \frac{(m^n - m^{n-1}, m^n - m^{n-1})}{(g_i(m_n) - g_i(m_{n-1}), m^n - m^{n-1})}$.
         iii. Update $m_{n+1} = m_n - a_i^n g_i(m_n)$.
      (d) Output $m_i^{k+1} = m_{N_1}$.
      2. Update $s^{k+1}$ by solving $$\min_s \frac{1}{2} \| B((1-U) \cdot s) - \hat{b} \|_F^2 + \lambda_2 TV((1-U) \cdot s)$$

where $b = b - \Sigma_{i=1}^p B_i(U \cdot m_i^{k+1})$.
      (a) Initial $s_0 = s^k$ and $\beta^0$.
      (b) $s_1 = s_0 - \beta^0((1-U)^T \cdot (B^T(B((1-U) \cdot s_0) - \hat{b})) + \lambda_2(1-U)^T \cdot \nabla TV_c((1-U) \cdot s_0))$.
      (c) For $b = 1, \ldots, N_2$:
         i. Calculate $g(s_n) = (1-U)^T \cdot (B^T(B((1-U) \cdot s_n) - \hat{b})) + \lambda_2(1-U)^T \cdot \nabla TV_c((1-U) \cdot s_n)$.
         ii. Calculate $\beta^n = \frac{(s_n - s_{n-1}, s_n - s_{n-1})}{(g_i(s_n) - g(s_{n-1}), s_n - s_{n-1})}$.
         iii. Update $s_{n+1} = s_n - \beta^n g(s_n)$.
      (d) Output $s^{k+1} = s_{N_2}$.

Output: Output $x_i = U \cdot m_i + (1 - U) \cdot s$

REFERENCES

The following references are incorporated herein by reference in their entireties:

[1] D. A. Jaffray, "Emergent technologies for 3-dimensional image-guided radiation delivery," Semin. Radiat. Oncol. 15, 208-216 (2005).

[2] D. A. Jaffray, J. H. Siewerdsen, J. W. Wong, A. A. Martinez, "Flat-panel cone-beam computed tomography for image-guided radiation therapy," Int. J. Radiat. Oncol., Biol., Phys. 53, 1337-1349 (2002).

[3] J. P. Bissonnette, T. G. Purdie, J. A. Higgins, W. Li, A. Bezjak, "Cone-beam computed tomographic image guidance for lung cancer radiation therapy," Int. J. Radiat. Oncol., Biol., Phys. 73, 927-934 (2009).

[4] L. A. Dawson, D. A. Jaffray, "Advances in image-guided radiation therapy," J. Clin. Oncol. 25, 938-946 (2007).

[5] L. Xing, B. Thorndyke, E. Schreibmann, Y. Yang, T. F. Li, G. Y. Kim, G. Luxton, A. Koong, "Overview of image-guided radiation therapy," Med. Dosim. 31, 91-112 (2006).

[6] W. Fu, Y. Yang, N. J. Yue, D. E. Heron, M. S. Huq, "A cone beam CT-guided online plan modification technique to correct interfractional anatomic changes for prostate cancer IMRT treatment," Phys. Med. Biol. 54, 1691-1703 (2009).

[7] J. Hatton, B. McCurdy, P. B. Greer, "Cone beam computerized tomography: the effect of calibration of the Hounsfield unit number to electron density on dose calculation accuracy for adaptive radiation therapy," Phys. Med. Biol. 54, N329-346 (2009).

[8] J. C. Park, S. H. Park, J. H. Kim, S. M. Yoon, S. S. Kim, J. S. Kim, Z. Liu, T. Watkins, W. Y. Song, "Four-dimensional cone-beam computed tomography and digital tomosynthesis reconstructions using respiratory signals extracted from transcutaneously inserted metal markers for liver SBRT," Med. Phys. 38, 1028-1036 (2011).

[9] J. C. Park, S. H. Park, J. H. Kim, S. M. Yoon, S. Y. Song, Z. Liu, B. Song, K. Kauweloa, M. J. Webster, A. Sandhu, L. K. Mell, S. B. Jiang, A. J. Mundt, W. Y. Song, "Liver motion during cone beam computed tomography guided stereotactic body radiation therapy," Med. Phys. 39, 6431-6442 (2012).

[10] S. Yoo, F. F. Yin, "Dosimetric feasibility of cone-beam CT-based treatment planning compared to CT-based treatment planning," Int. J. Radiat. Oncol., Biol., Phys. 66, 1553-1561 (2006).

[11] C. D. Fuller, T. J. Scarbrough, J. J. Sonke, C. R. Rasch, M. Choi, J. Y. Ting, S. J. Wang, N. Papanikolaou, D. I. Rosenthal, "Method comparison of automated matching software-assisted cone-beam CT and stereoscopic kilovoltage x-ray positional verification image-guided radiation therapy for head and neck cancer: a prospective analysis," Phys. Med. Biol. 54, 7401-7415 (2009).

[12] F. Xu, J. Wang, S. Bai, Y. Li, Y. Shen, R. Zhong, X. Jiang, Q. Xu, "Detection of intrafractional tumour position error in radiotherapy utilizing cone beam computed tomography," Radiother. Oncol. 89, 311-319 (2008).

[13] L. Dietrich, S. Jetter, T. Tucking, S. Nill, U. Oelfke, "Linac-integrated 4D cone beam CT: first experimental results," Phys. Med. Biol. 51, 2939-2952 (2006).

[14] S. Kriminski, M. Mitschke, S. Sorensen, N. M. Wink, P. E. Chow, S. Tenn, T. D. Solberg, "Respiratory correlated cone-beam computed tomography on an isocentric C-arm," Phys. Med. Biol. 50, 5263-5280 (2005).

[15] T. Li, L. Xing, P. Munro, C. McGuinness, M. Chao, Y. Yang, B. Loo, A. Koong, "Four-dimensional cone-beam computed tomography using an on-board imager," Med. Phys. 33, 3825-3833 (2006).

[16] J. J. Sonke, L. Zijp, P. Remeijer, M. van Herk, "Respiratory correlated cone beam CT," Med. Phys. 32, 1176-1186 (2005).

[17] J. Cai, P. W. Read, K. Sheng, "The effect of respiratory motion variability and tumor size on the accuracy of average intensity projection from four-dimensional computed tomography: an investigation based on dynamic MRI," Med. Phys. 35, 4974-4981 (2008).

[18] J. J. Sonke, J. Lebesque, M. van Herk, "Variability of four-dimensional computed tomography patient models," Int. J. Radiat. Oncol., Biol., Phys. 70, 590-598 (2008).

[19] N. Clements, T. Kron, R. Franich, L. Dunn, P. Roxby, Y. Aarons, B. Chesson, S. Siva, D. Duplan, D. Ball, "The effect of irregular breathing patterns on internal target volumes in four-dimensional CT and cone-beam CT images in the context of stereotactic lung radiotherapy," Med. Phys. 40, 021904 (2013).

[20] K. Nakagawa, A. Haga, S. Kida, Y. Masutani, H. Yamashita, W. Takahashi, A. Sakumi, N. Saotome, T. Shiraki, K. Ohtomo, Y. Iwai, K. Yoda, "4D registration and 4D verification of lung tumor position for stereotactic volumetric modulated arc therapy using respiratory-correlated cone-beam CT," J. Radiat. Res. 54, 152-156 (2013).

[21] J. J. Sonke, M. Rossi, J. Wolthaus, M. van Herk, E. Damen, J. Belderbos, "Frameless stereotactic body radiotherapy for lung cancer using four-dimensional cone beam CT guidance," Int. J. Radiat. Oncol., Biol., Phys. 74, 567-574 (2009).

[22] L. A. Feldkamp, L. C. Davis, J. W. Kress, "Practical Cone-Beam Algorithm," J. Opt. Soc. Am. A. 1, 612-619 (1984).

[23] D. J. Brenner, C. D. Elliston, "Estimated radiation risks potentially associated with full-body CT screening," Radiology 232, 735-738 (2004).

[24] G. Brix, S. Nissen-Meyer, U. Lechel, J. Nissen-Meyer, J. Griebel, E. A. Nekolla, C. Becker, M. Reiser, "Radiation exposures of cancer patients from medical X-rays: how relevant are they for individual patients and population exposure?," Eur. J. Radiol. 72, 342-347 (2009).

[25] E. J. Hall, "Lessons we have learned from our children: cancer risks from diagnostic radiology," Pediatr. Radiol. 32, 700-706 (2002).

[26] F. Bergner, T. Berkus, M. Oelhafen, P. Kunz, T. Pan, M. Kachelriess, "Autoadaptive phase-correlated (AAPC) reconstruction for 4D CBCT," Med. Phys. 36, 5695-5706 (2009).

[27] T. Li, A. Koong, L. Xing, "Enhanced 4D cone-beam CT with inter-phase motion model," Med. Phys. 34, 3688-3695 (2007).

[28] Q. Zhang, Y. C. Hu, F. Liu, K. Goodman, K. E. Rosenzweig, G. S. Mageras, "Correction of motion artifacts in cone-beam CT using a patient-specific respiratory motion model," Med. Phys. 37, 2901-2909 (2010).

[29] G. H. Chen, J. Tang, S. Leng, "Prior image constrained compressed sensing (PICCS): a method to accurately reconstruct dynamic CT images from highly undersampled projection data sets," Med. Phys. 35, 660-663 (2008).

[30] X. Jia, Z. Tian, Y. Lou, J. J. Sonke, S. B. Jiang, "Four-dimensional cone beam CT reconstruction and enhancement using a temporal nonlocal means method," Med. Phys. 39, 5592-5602 (2012).

[31] P. T. Lauzier, G. H. Chen, "Characterization of statistical prior image constrained compressed sensing. I. Applications to time-resolved contrast-enhanced CT," Med. Phys. 39, 5930-5948 (2012).

[32] S. Leng, J. Zambelli, R. Tolakanahalli, B. Nett, P. Munro, J. Star-Lack, B. Paliwal, G. H. Chen, "Streaking artifacts reduction in four-dimensional cone-beam computed tomography," Med. Phys. 35, 4649-4659 (2008).

[33] X. C. Pan, E. Y. Sidky, M. Vannier, "Why do commercial CT scanners still employ traditional, filtered back-projection for image reconstruction?," Inverse. Probl. 25 (2009).

[34] G. H. Chen, J. Tang, S. Leng, "Prior Image Constrained Compressed Sensing (PICCS)," Proc. Soc. Photo. Opt. Instrum. Eng. 6856, 685618 (2008).

[35] P. T. Lauzier, G. H. Chen, "Characterization of statistical prior image constrained compressed sensing (PICCS): II. Application to dose reduction," Med. Phys. 40, 021902 (2013).

[36] S. Leng, J. Tang, J. Zambelli, B. Nett, R. Tolakanahalli, G. H. Chen, "High temporal resolution and streak-free four-dimensional cone-beam computed tomography," Phys. Med. Biol. 53, 5653-5673 (2008).

[37] M. G. Lubner, P. J. Pickhardt, J. Tang, G. H. Chen, "Reduced image noise at low-dose multidetector CT of the abdomen with prior image constrained compressed sensing algorithm," Radiology 260, 248-256 (2011).

[38] B. Nett, J. Tang, S. Leng, G. H. Chen, "Tomosynthesis via Total Variation Minimization Reconstruction and Prior Image Constrained Compressed Sensing (PICCS) on a C-arm System," Proc. Soc. Photo. Opt. Instrum. Eng. 6913, nihpa92672 (2008).

[39] J. C. Ramirez-Giraldo, J. Trzasko, S. Leng, L. Yu, A. Manduca, C. H. McCollough, "Nonconvex prior image constrained compressed sensing (NCPICCS): theory and simulations on perfusion CT," Med. Phys. 38, 2157-2167 (2011).

[40] B. Song, J. C. Park, W. Y. Song, "A low-complexity 2-point step size gradient projection method with selective function evaluations for smoothed total variation based CBCT reconstructions," Phys. Med. Biol. 59, 6565-6582 (2014).

[41] T. P. Szczykutowicz, G. H. Chen, "Dual energy CT using slow kVp switching acquisition and prior image constrained compressed sensing," Phys. Med. Biol. 55, 6411-6429 (2010).

[42] J. Tang, B. E. Nett, G. H. Chen, "Performance comparison between total variation (TV)-based compressed sensing and statistical iterative reconstruction algorithms," Phys. Med. Biol. 54, 5781-5804 (2009).

[43] J. C. Park, J. S. Kim, S. H. Park, Z. W. Liu, B. Y. Song, W. Y. Song, "Motion-map constrained image reconstruction (MOR): Application to four-dimensional cone-beam computed tomography," Med. Phys. 402013).

[44] J. Barzilai, J. M. Borwein, "2-Point Step Size Gradient Methods," Ima. J. Numer. Anal. 8, 141-148 (1988).

[45] M. A. T. Figueiredo, R. D. Nowak, S. J. Wright, "Gradient Projection for Sparse Reconstruction: Application to Compressed Sensing and Other Inverse Problems," IEEE. J. Sel. Top. Signal Process. 1, 586-597 (2007).

[46] J. C. Park, S. H. Park, J. S. Kim, Y. Han, M. K. Cho, H. K. Kim, Z. Liu, S. B. Jiang, B. Song, W. Y. Song, "Ultra-fast digital tomosynthesis reconstruction using general-purpose GPU programming for image-guided radiation therapy," Technol. Cancer Res. T. 10, 295-306 (2011).

[47] J. C. Park, B. Y. Song, J. S. Kim, S. H. Park, H. K. Kim, Z. W. Liu, T. S. Suh, W. Y. Song, "Fast compressed sensing-based CBCT reconstruction using Barzilai-Borwein formulation for application to on-line IGRT," Med. Phys. 39, 1207-1217 (2012).

[48] H. Yan, X. Zhen, M. Folkerts, Y. Li, T. Pan, L. Cervino, S. B. Jiang, X. Jia, "A hybrid reconstruction algorithm for fast and accurate 4D cone-beam CT imaging," Med. Phys. 41, 071903 (2014).

[49] F. Bergner, T. Berkus, M. Oelhafen, P. Kunz, T. Pa, R. Grimmer, L. Ritschl, M. Kachelriess, "An investigation of 4D cone-beam CT algorithms for slowly rotating scanners," Med. Phys. 37, 5044-5053 (2010).

[50] G. C. Mc Kinnon, R. H. Bates, "Towards imaging the beating heart usefully with a conventional CT scanner," IEEE Trans. Biomed. Eng. 28, 123-127 (1981).

[51] T. Niu, X. Ye, Q. Fruhauf, M. Petrongolo, L. Zhu, "Accelerated barrier optimization compressed sensing (ABOCS) for CT reconstruction with improved convergence," Phys. Med. Biol. 59, 1801-1814 (2014).

[52] T. Niu, L. Zhu, "Accelerated barrier optimization compressed sensing (ABOCS) reconstruction for cone-beam CT: phantom studies," Med. Phys. 39, 4588-4598 (2012).

[53] J. Wang, H. Guan, T. Solberg, "Inverse determination of the penalty parameter in penalized weighted least-squares algorithm for noise reduction of low-dose CBCT," Med. Phys. 38, 4066-4072 (2011).

[54] L. Zhu, L. Xing, "Search for IMRT inverse plans with piecewise constant fluence maps using compressed sensing techniques," Med. Phys. 36, 1895-1905 (2009).

Computing Environment

Figure 3:
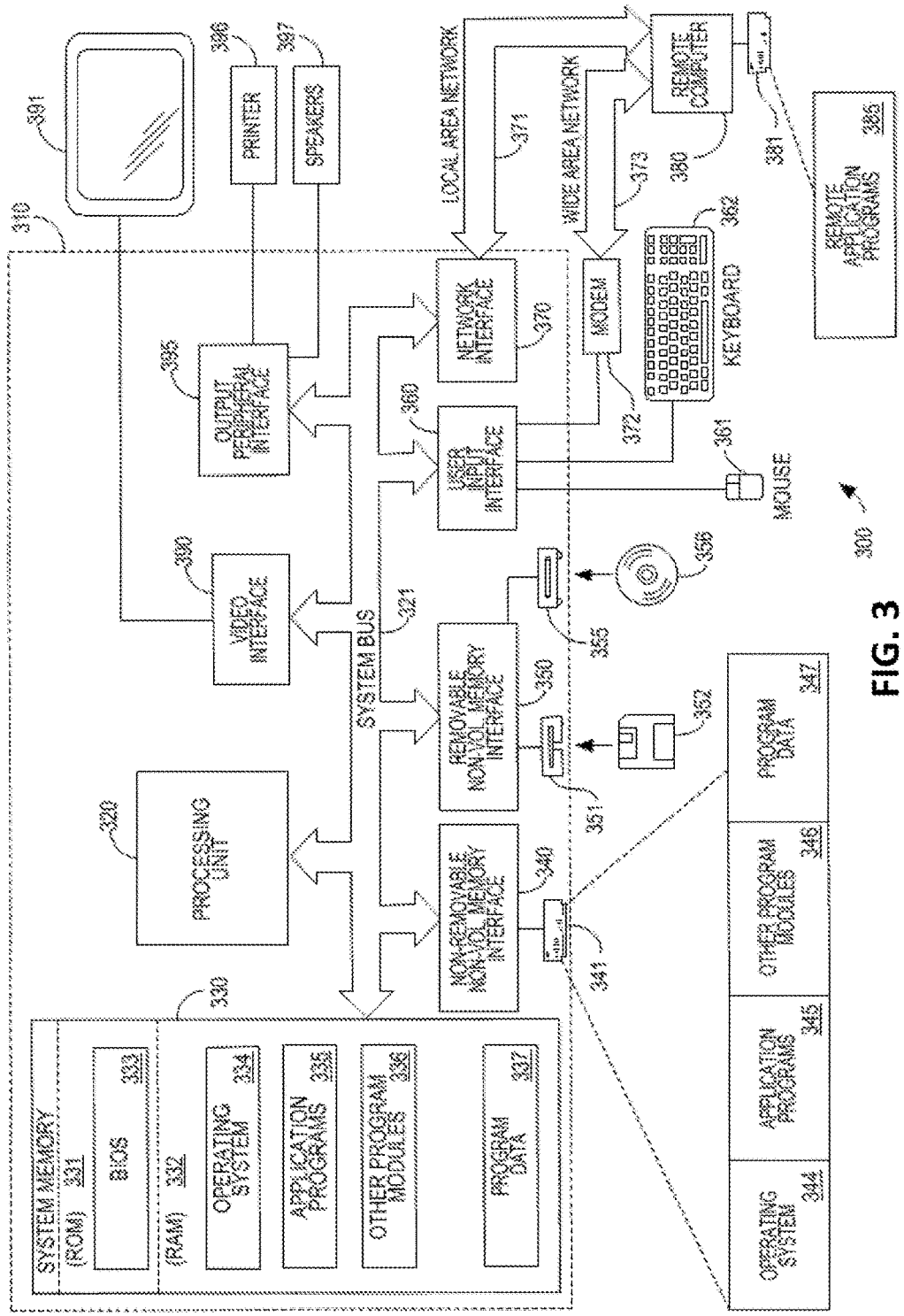
FIG. 3 is a diagram illustrating a computer system on which some embodiments may be implemented.

Techniques as described herein may be implemented on any suitable hardware, including a programmed computing system. For example, image reconstruction may be performed by programming a computing device. Similarly, image reconstruction may be controlled by a programmed computing device. FIG. 1 illustrates a system implemented with one or multiple computing devices, which may be distributed and/or centralized. Also, FIG. 2 illustrates an algorithm executing on at least one computing device. FIG. 3 illustrates an example of a suitable computing system environment 300 on which embodiments of this algorithm may be implemented. This computing system may be representative of a computing system that implements the techniques described herein. However, it should be appreciated that the computing system environment 300 is only one example of a suitable computing environment and is not intended to suggest any limitation as to the scope of use or functionality of the invention. Neither should the computing environment 300 be interpreted as having any dependency or requirement relating to any one or combination of components illustrated in the exemplary operating environment 300.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 3, an exemplary system for implementing the invention includes a general purpose computing device in the form of a computer 310. Though a programmed general purpose computer is illustrated, it should be understood by one of skill in the art that algorithms may be implemented in any suitable computing device. Accordingly, techniques as described herein may be implemented in a system for image reconstruction. These techniques may be implemented in such controllers as originally manufactured or as a retrofit, such as by changing program memory devices holding programming for such controllers or software download. Thus, some or all of the components illustrated in FIG. 3, though illustrated as part of a general purpose computer, may be regarded as representing portions of a controller or other component in an image reconstruction system.

Components of computer 310 may include, but are not limited to, a processing unit 320, a system memory 330, and a system bus 321 that couples various system components including the system memory 330 to the processing unit 320. The system bus 321 may be any of several types of bus structures including a memory bus or memory controller, a peripheral bus, and a local bus using any of a variety of bus architectures. By way of example and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 310 typically includes a variety of computer readable media. Computer readable media can be any available media that can be accessed by computer 310 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by computer 310. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example and not limitation, communication media includes wired media such as a wired network or direct-wired connection, and wireless media such as acoustic, radio frequency (RF), infrared (IR), and other wireless media. Combinations of any of the above should also be included within the scope of computer readable media.

The system memory 330 includes computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to and/or presently being operated on by processing unit 320. By way of example and not limitation, FIG. 3 illustrates operating system 334, application programs 335, other program modules 336, and program data 337.

The computer 310 may also include other removable/non-removable, volatile/nonvolatile computer storage media. By way of example only, FIG. 3 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 is typically connected to the system bus 321 through an non-removable memory interface such as interface 340, and magnetic disk drive 351 and optical disk drive 355 are typically connected to the system bus 321 by a removable memory interface, such as interface 350.

The drives and their associated computer storage media discussed above and illustrated in FIG. 3, provide storage of computer readable instructions, data structures, program modules, and other data for the computer 310. In FIG. 3, for example, hard disk drive 341 is illustrated as storing operating system 344, application programs 345, other program modules 346, and program data 347. Note that these components can either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as a keyboard 362 and pointing device 361, commonly referred to as a mouse, trackball, or touch pad. Other input devices (not shown) may include a microphone, joystick, game pad, satellite dish, scanner, or the like. These and other input devices are often connected to the processing unit 320 through a user input interface 360 that is coupled to the system bus, but may be connected by other interface and bus structures, such as a parallel port, game port, or a universal serial bus (USB). A monitor 391 or other type of display device is also connected to the system bus 321 via an interface, such as a video interface 390. In addition to the monitor, computers may also include other peripheral output devices such as speakers 397 and printer 396, which may be connected through an output peripheral interface 395.

The computer 310 may operate in a networked environment using logical connections to one or more remote computers, such as a remote computer 380. The remote computer 380 may be a personal computer, a server, a router, a network PC, a peer device, or some other common network node, and typically includes many or all of the elements described above relative to the computer 310, although only a memory storage device 381 has been illustrated in FIG. 3. The logical connections depicted in FIG. 3 include a local area network (LAN) 371 and a wide area network (WAN) 373, but may also include other networks. Such networking environments are commonplace in offices, enterprise-wide computer networks, intranets, and the Internet.

When used in a LAN networking environment, the computer 310 is connected to the LAN 371 through a network interface or adapter 370. When used in a WAN networking environment, the computer 310 typically includes a modem 372 or other means for establishing communications over the WAN 373, such as the Internet. The modem 372, which may be internal or external, may be connected to the system bus 321 via the user input interface 360, or other appropriate mechanism. In a networked environment, program modules depicted relative to the computer 310, or portions thereof, may be stored in the remote memory storage device. By way of example and not limitation, FIG. 3 illustrates remote application programs 385 as residing on memory device 381. It will be appreciated that the network connections shown are exemplary and other means of establishing a communications link between the computers may be used.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A system for constructing a plurality of images representing a four-dimensional computed tomography sequence of an object from a plurality of projections, the projections being taken from a plurality of angles with respect to the object and at a plurality of times, first portions of the object being less static than second portions of the object, the system comprising:
at least one processor configured to:
iteratively process projections of the plurality of projections for a plurality of groups, each group of the plurality of groups comprising projections collected while the first portions of the object are in corresponding locations, with each iteration comprising:
reconstructing first image portions representing the first portions of the object, the reconstructing of each first image portion of the first image portions being based on projections in a respective group of the plurality of groups; and
reconstructing a second image portion, the second image portion representing the second portions of the object, based on projections in multiple groups of the plurality of groups and on the reconstructed first image portions.

2. A method for constructing a plurality of images representing a four-dimensional computed tomography sequence of an object from a plurality of projections, the projections being taken from a plurality of angles with respect to the object and at a plurality of times, first portions of the object being less static than second portions of the object, the method comprising:
using at least one processor:
iteratively processing projections of the plurality of projections for a plurality of groups, each group of the plurality of groups comprising projections collected while the first portions of the object are in corresponding locations, with each iteration comprising:
reconstructing first image portions representing the first portions of the object, the reconstructing of each first image portion of the first image portions being based on projections in a respective group of the plurality of groups; and
reconstructing a second image portion, the second image portion representing the second portions of the object, based on projections in multiple groups of the plurality of groups and on the reconstructed first image portions.

3. A computer-readable storage medium encoded with executable instructions that, when executed by at least one processor, cause the at least one processor to perform a method for constructing a plurality of images representing a four-dimensional computed tomography sequence of an object from a plurality of projections, the projections being taken from a plurality of angles with respect to the object and at a plurality of times, first portions of the object being less static than second portions of the object, the method comprising:
using at least one processor:
iteratively processing projections of the plurality of projections for a plurality of groups, each group of the plurality of groups comprising projections collected while the first portions of the object are in corresponding locations, with each iteration comprising:
reconstructing first image portions representing the first portions of the object, the reconstructing of each first image portion of the first image portions being based on projections in a respective group of the plurality of groups; and
reconstructing a second image portion, the second image portion representing the second portions of the object, based on projections in multiple groups of the plurality of groups and on the reconstructed first image portions.

4. The system of claim 1, wherein:
each group of the plurality of groups corresponds to one or more locations of the locations.

5. The system of claim 1, wherein:
each group of the plurality of groups corresponds to one or more times of the plurality of times.

6. The system of claim 1, wherein:
the at least one processor is further configured to:
compute a common-mask based on differences between a three-dimensional computed tomography volume and a four-dimensional computed tomography volume; and
apply the common-mask to obtain an initial solution of reconstructing the first image portions and an initial solution of reconstructing the second image portion.

7. The method of claim 2, the method further comprising:
computing a common-mask based on differences between a three-dimensional computed tomography volume and a four-dimensional computed tomography volume; and
applying the common-mask to obtain an initial solution of reconstructing the first image portions and an initial solution of reconstructing the second image portion.

8. The system of claim 1, wherein:
the at least one processor is further configured to:
for each group of the plurality of groups, combine a solution of reconstructing the first image portions with a solution of reconstructing the second image portion to produce a constructed image for the group; and
sequence each constructed image for each group of the plurality of groups to produce a series of constructed images.

9. The method of claim 2, the method further comprising:
for each group of the plurality of groups, combining a solution of reconstructing the first image portions with a solution of reconstructing the second image portion to produce a constructed image for the group; and
sequencing each constructed image for each group of the plurality of groups to produce a series of constructed images.

10. The system of claim 1, wherein:
the at least one processor comprises at least one graphics processing unit for reconstructing the first image portions and reconstructing the second image portion in parallel.

11. The system of claim 1, wherein:
the first image portions comprise a plurality of motion components of the plurality of images; and
the second image portion comprises one or more static components of the plurality of images.

12. The system of claim 11, wherein:
the one or more static components comprise a common static component of the plurality of images.

13. The system of claim 1, wherein:
for at least one iteration:
reconstructing the first image portions is based on a previous solution of reconstructing the second image portion.

14. The system of claim 1, wherein:
the at least one processor is further configured to:
iteratively process the projections for about 60 iterations or less.

15. The method of claim 2, wherein:
iteratively processing the projections comprising iteratively process the projections for about 60 iterations or less.

16. The system of claim 1, wherein:
the four-dimensional computed tomography sequence of the object comprises a four-dimensional cone-beam computed tomography sequence of the object.

17. The method of claim 2, wherein:
each group of the plurality of groups corresponds to one or more locations of the locations.

18. The computer-readable storage medium of claim 3, wherein:
each group of the plurality of groups corresponds to one or more times of the plurality of times.

19. The computer-readable storage medium of claim 3, the method further comprising:
computing a common-mask based on differences between a three-dimensional computed tomography volume and a four-dimensional computed tomography volume; and
applying the common-mask to obtain an initial solution of reconstructing the first image portions and an initial solution of reconstructing the second image portion.

20. The computer-readable storage medium of claim 3, the method further comprising:
for each group of the plurality of groups, combining a solution of reconstructing the first image portions with a solution of reconstructing the second image portion to produce a constructed image for the group; and
sequencing each constructed image for each group of the plurality of groups to produce a series of constructed images.

* * * * *